(12) United States Patent
Nguyen et al.

(10) Patent No.: US 7,799,552 B2
(45) Date of Patent: Sep. 21, 2010

(54) PROTEIN AND NUCLEIC ACID EXPRESSION SYSTEMS

(75) Inventors: Hiep-Hoa T. Nguyen, Santa Ana, CA (US); Sunney I. Chan, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 397 days.

(21) Appl. No.: 10/210,895

(22) Filed: Jul. 22, 2002

(65) Prior Publication Data

US 2003/0032141 A1 Feb. 13, 2003

Related U.S. Application Data

(60) Provisional application No. 60/306,811, filed on Jul. 20, 2001.

(51) Int. Cl.
*C12N 1/21* (2006.01)
*C12P 21/00* (2006.01)
*C12N 15/09* (2006.01)
*C12N 15/74* (2006.01)

(52) U.S. Cl. ............... 435/253.1; 435/320.1; 435/69.1; 435/71.2; 435/471; 536/23.1; 536/24.1

(58) Field of Classification Search ............... 435/320.1, 435/69.1, 252.3; 536/23.1, 24.1
See application file for complete search history.

(56) References Cited

U.S. PATENT DOCUMENTS

| 5,316,940 A | | 5/1994 | Georgiou et al. | |
| 5,830,475 A | * | 11/1998 | Aldovini et al. | ............ 424/200.1 |
| 5,958,757 A | | 9/1999 | Steffan et al. | |
| 6,258,565 B1 | * | 7/2001 | Blatny et al. | ............... 435/71.2 |

FOREIGN PATENT DOCUMENTS

| EP | 1 010 757 A2 | | 6/2000 |
| WO | WO 00/09715 A1 | | 2/2000 |
| WO | WO02/055549 | * | 7/2002 |

OTHER PUBLICATIONS

Imaeda and Ogura, Formation of Intracytoplasmic membrane system of Mycobacteria related to cell division, JBC, 1963, vol. 85, pp. 150-163.*
Heidmann et al, FLexibility and Interchangeability of Polyadenylation Signals in *Saccharomyces cerevisiae*, MCB, 1994, vol. 14, No. 7, pp. 4633-4642.*

De Maeyer et al, Expression of a chemically synthesized human a1 interferon gene, Proc. Natl Acad. Sci. USA vol. 79, pp. 4256-4259, Jul. 1982.*
Lesk et al, Prediction of Protein Function from Protein Sequence and Structure, p. 27 and 28, downloaded Sep. 16, 2007.*
Guo et al, Protein tolerance to random amino acid change, PNAS, 2004, vol. 101 (25), pp. 9205-9210.*
Figueira, M. M., et al. Production of green fluorescent protein by the methylotrophic bacterium Methylobacterium extorquens. FEMS Microbiology Letters. 193, 195-200 (2000).
Gilbert, B. et al. Molecular Analysis of the pmo (Particulate Methane Monooxygenase) Operons from Two Type II Methanotrophs. App. and Env. Microbiology. pp. 966-975 (2000).
Jahng, D. et al. Trichloroethylene Degradation Using Recombinant Bacteria Expressing Soluble Methane Mono-oxygenase from *Methylosinus trichosporium* OB3b. Molecular Biology of Pseudomonads. 5th International Symposium on Pseusomonads, Molecular Biology and Biotechnology, Jan. 11, 1997. pp. 280-288.
Nguyen, H. et al, The Particulate Methane Monooxygenase from *Methylococcus capsulatus* (Bath) Is a Novel Copper-containing Three-subunit Enzyme. J. of Bio. Chem. 473:14, 7957-966 (1998).
Semrau, J.D. et al. Particulate Methane Monooxygenase Genes in Methanotrophs. Journal of Bacteriology. 177(11), 3071-79 (1995).
Stolyar, S. et al. Expression of Individual Copies of *Methylococcus capsulatus* Bath Particulate Methane Monooxygenase Genes. Journal of Bacteriology. 183(5), 1810-12.
Stolyar, S. et al. Role of multiple gene copies in particulate methane monooxygenase activity in the methane-oxidizing bacterium *Methylococcus capsulatus* Bath. Microbiology, 145:1235-44 (1999).
EP 02 75 2649, May 6, 2005, European Search Report.
Berson and Lidstrom 1997 FEMS Microbiol Letters (148):169-174.
Cardy and Murrell 1990 J Gen microbial (136): 343-352.
Chistoerdova et al. 1994 FEMS Microbiol Lett (121): 343-348.
Csáki et al. 2001 FEMS Microbiol Letters (205): 203-207.
Lloyd et al. 1999 Microbiology (145): 461-470.
Tyutikov et al. 1980 J Bacteriology (144): 375-381.
Waechter-Brulla et al. 1993 J Bacteriology (175): 3767-3775.
Wu et al. 2000 Arch Microbiol (173): 319-324).
Stolyar, S. et al. Expression of Individual Copies of *Methylococcus capsulatus* Bath Particulate Methane Monooxygenase Genes. Journal of Bacteriology. 183(5), 1810-12, 2001.

* cited by examiner

*Primary Examiner*—Maria Marvich
(74) *Attorney, Agent, or Firm*—McCarter & English, LLP; Elizabeth A. Hanley; Yu Lu

(57) ABSTRACT

Among the inventions disclosed herein are: nucleic acid expression systems for bacteria having an intracytoplasmic membrane system, including, for example, methanotrophic bacteria; recombinant nucleic acid constructs comprising a pmo promoter operably linked to an expressible nucleic acid; cloning vectors suitable for making recombinant nucleic acid constructs and methods for the production of proteins such as membrane proteins.

30 Claims, 4 Drawing Sheets

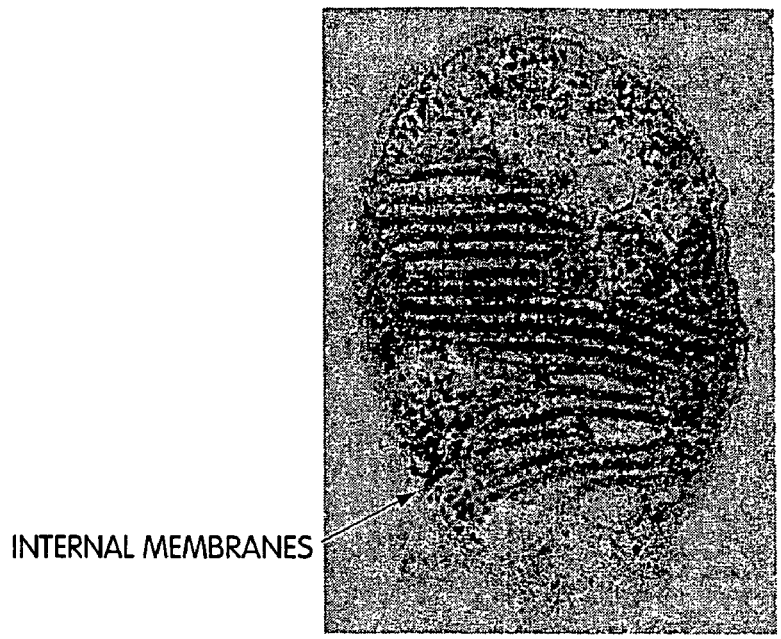

INTERNAL MEMBRANES

Fig. 1

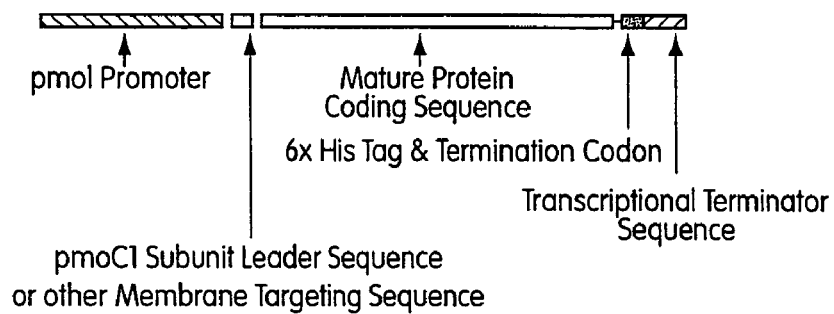

pmo Promoter | pmoC1 Subunit Leader Sequence or other Membrane Targeting Sequence | Mature Protein Coding Sequence | 6x His Tag & Termination Codon | Transcriptional Terminator Sequence

Fig. 2

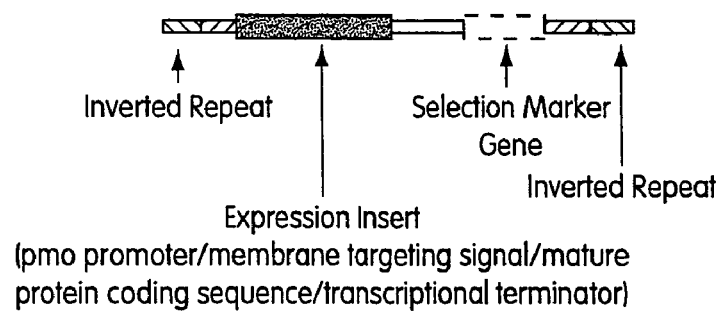

Inverted Repeat | Expression Insert (pmo promoter/membrane targeting signal/mature protein coding sequence/transcriptional terminator) | Selection Marker Gene | Inverted Repeat

Fig. 3 pmoC1 upstream sequence

```
   1 gtcgactggg caccagccgg atgcgtccgt caaccccgac tgttccgcca agaactccgg
  61 ccttctgtgg cgggatgacg ttgagcacat cggcacagaa agtgtcgaac tcggtttcga
 121 cggttcgccc ggcggcatcg atccgctcca gccgtccctc tttttccgag gaaacccatt
 181 ccaccatgtc tccgtagagt tcgcgccagg cctgctcgaa tgccggctgc ttggaaaacc
 241 gggtcttggc atcgagtatc aggatcttgg agcggggttt gtgcttttc atgtaatagg
 301 cgatgagcga ggcgcgttcg taggggccag gcggacaacg atagggagaa ggtggtgcgg
 361 tgatcagaac caggccgccg tcgggcatcg cgcggatctg ccgggcgagc aaagcggtct
 421 gggggccggc cttccaggca tggggaacga accggctcgc cgcctcgtca tagcccatta
 481 tcgcctccca gcgaaagtcg atgccggggg agaggactag cctgtcgtag gtgacctcgg
 541 caccatcgtt cagtatcaca cgccgtcgct gccgatccag gcgggcgacc cgggcggtta
 601 cctttcctat atccagctcc cgccgcaacc agtcataaga ccgcgcgaga gtccccatgt
 661 ccccgaggcc ggcgactgct tcgttcgatc cggggcagga aagataagtc tcctgcggtt
 721 cgatcaatgt gatcgtcaga ccgggattca tctgcttcag atagcgggcg gccgtggcac
 781 cgccataacc gccaccgacg accacgaccg gccgcctgag cgaagacctt gccggaagcg
 841 cagccaccca gtcccagccc atgccgcaga ctgccagcag gcgcaggaac cgccgccggc
 901 ggatcatggc ctctttccca gaaagccggc gatcgcttca atgtcctggt tcgtgagtcc
 961 ggcagcgatc cggttcatga ccgtgcccga tcttttcct tcacggtact cccgcaacag
1021 agatgccatc tccttcgcat cgaagcggcg taacgatgcc ggttcgggaa tctgctcctc
1081 ctcgtcggca tggcagccga ggcaaccgag cgcagccaaa accatgtccg gtttttcggc
1141 ccgggccggg aaacagagag cgacagcgat cgtaccgatc tggacgcgtc tcacaaacga
1201 caaaacgtca cgatgggtgt tcggtagctg agtcacgggg atttgtagaa gtataggacc
1261 gacggatttt atgcaagcat gtcgctttga ccaagccggg attccatgga agggatgtca
1321 tcgggagagt tatttatgtc gttgatttat aagaaactac ccctgcgtca aatgtcgca
1381 gattttttc  tt gacagtttgg gggagggtga tagatcctcc accg a tggac cggtaccgcc
1441 tctgttgcgg ggtccatgaa atgcccgtta gaggcagaac cgatagggaa ttagagaagc
1501 gggcgtcggc gccgaatgcc ggccctgtc aaccatcact ttaggaggaa caaaca (SEQ ID NO:4)
```

Fig. 4 pmoC1 membrane targeting leader sequence
atg gca gca aca acc att ggt ggt gca gct gcg gcg gaa gcg ccg ctg ctg gac aag
aag tgg ctc acg ttc gca ctg gcg att tac acc (SEQ ID NO:5)
Translated Sequence: MAATTIGGAAAAEAPLLDKKWLTFALAIYT (SEQ ID NO: 3)
Short Form Translated Sequence: MAATTIGGAAAAEAAPLLDKK (SEQ ID NO:10

Fig. 5A

Flavobacterium organophosphate lyase membrane targeting leader sequence.
MQTRRVVLKSAAAGTLLGGLAGCASVAG (SEQ ID NO:9)

Fig. 5B

3'-flanking region of the pmo1 locus containing the pmo1 transcriptional terminator:

4501 tttcgccggt ctgctgttct tcttcgacgc cactggcaac cgccaggtcg tccagatcga
4561 cgcaccgctg atcccgtcgt tcatgtaatc gcctggggga gtccttcggg actccccagc
4621 cggcggtcaa cgccaaaacc cccggccggc aacggtcggg ggttttttat tctggtctgg
4681 ttttgtgttc (SEQ ID NO: 6)

Fig. 6

Sequence of the 5'-upstream of the pmoC2 containing the pmo2 promoter 3382 aatcctgct ggtcgcttga ccctcgtgtc cggcgtacgc
3421 cggacacgat cacggtctgt cgcaagcccg cttgttgatc tggactcctt cccagaacga
3481 gcgcagcgga gcctcccgtt ccgcgccgtc cattctcttt ttcatccaag tgcccggctc
3541 atgaggtcgg ctcacgaggc tgag *cctgcg tcaaaatgac gcagatttttc ctgacagcc*
3601 *tcgggttggg tgatagact* g cgaccca cca aggggccggc caacccgtgg gcgcggctct
3661 gaggggcggc aagg (SEQ ID NO:7)

a: Transcriptional start site
Underline sequence: promoter and regulatory sequence

Fig. 7

The 3'-flanking region of the pmo2 locus containing the pmo2 transcriptional terminator sequence 6794 tcgcctg ggggagtcct tcggggctcc cctgccggcg gtcaacgcca
6841 aaaccccgg ccggcaacgg tcggggggttt ttttatcggc tggatttaga cgttcagggg
6901 gcgacgatcg tcaagcaaca aggccccacc aggccggggc cttgtcgtcg agcgtcggcg
6961 gcgccgtcag ccctcggcgg ttcgcgaagc cttcttgcgc tcgtgttcct gcaggagctt
7021 cttgcggatg cgaatgctct gaggggtcac ttccacgagt tcatcgtcgt cgatgaattc (SEQ ID NO:8)

Fig. 8

PROTEIN AND NUCLEIC ACID EXPRESSION SYSTEMS

RELATED APPLICATIONS

This application claims the benefit of the filing date of U.S. Provisional Application No. 60/306,811, filed Jul. 20, 2001, and incorporated by reference herein in its entirety.

FUNDING

Work described herein was funded, in part, by the George Grant Hoag Professorship, grant DAAD19-02-06-0022 from Department of Defense, U.S. Army Research Office, and National Science Foundation SBIR grant #0215308. The United States government has certain rights in the invention.

BACKGROUND OF THE INVENTION

Membrane-bound proteins and enzymes (for instance channels, receptors, and transporters) are involved in critical cellular processes, yet our understanding of these important biological molecules at molecular levels lags behind those of soluble proteins. For example, while thousands of X-ray crystal structures of soluble proteins are known, only about 30 structures of unique membrane proteins are currently available. A significant barrier to the structural characterization of membrane proteins is that membrane proteins are generally synthesized at low levels in cells. Obtaining significant quantities (even at milligrams scale) of purified membrane proteins for biochemical and biophysical studies has been a major obstacle.

Systems that can afford very high yields of recombinant soluble proteins are ineffective for membrane protein expression. For example, the three most popular and powerful commercially available recombinant protein expression vehicles, the bacteria *Escherichia coli* with T7 phage promoter-driven plasmids, the baculovirus *Autograph californica* nuclear polyhedrosis virus in *Sporodoptera frugiperda* cell lines, and the methylotrophic yeast *Pichia pastoris* with the alcohol oxidase promoter-driven plasmids, work well only for soluble proteins. Many expression systems fail to provide good production of membrane proteins because they lack a powerful promoter and/or a suitable cellular compartment to house the recombinant membrane proteins at significant levels.

A membrane protein production system would be indispensable and would allow scientists to tackle many currently intractable problems in membrane protein biochemistry.

SUMMARY

In certain embodiments, the invention relates to the use of a bacterial cell having an intracytoplasmic membrane system for the expression and production of proteins and nucleic acids. In certain embodiments, the present invention relates to recombinant nucleic acids and expression constructs that comprise an expressible nucleic acid (a nucleic acid to be expressed in a bacterial cell having an intracytoplasmic membrane system) and regulatory sequences that function (are suitable for use in expressing the expressible nucleic acid) in a bacterial cell having an intracytoplasmic membrane system and are positioned such that expression (or a post-expression processing event, such as protein targeting) of the expressible nucleic acid is under control of the regulatory sequences. Optionally the regulatory sequences include a promoter, such as a pmo promoter or a viral promoter. Optionally, the regulatory sequences include a membrane-targeting sequence. Optionally, the regulatory sequences include a transcription stop site.

In certain embodiments, the invention relates to expression constructs comprising a membrane targeting sequence operably linked to an expressible nucleic acid and a promoter for expression of the expressible nucleic acid in a cell having an intracytoplasmic membrane system. Optionally the promoter is a pmo promoter, such as a promoter comprising a sequence shown in SEQ ID NO:1, SEQ ID NO:2, SEQ ID NO: 4, SEQ ID NO:7 or a functional variant thereof. Optionally the promoter is a viral promoter. In certain embodiments the expression of the expressible nucleic acid is stimulated by copper(II) ions. In certain embodiments, the promoter functions in methanotrophs or nitrifying bacteria. While the expressible nucleic acid may be any nucleic acid of interest, in certain embodiments the expressible nucleic acid encodes a polypeptide, and preferably a membrane protein. In additional embodiments, the membrane targeting sequence is functional to target a polypeptide encoded by the expressible nucleic acid to a membrane system. The membrane targeting sequence may target the polypeptide to a specific membrane system, such as the cytoplasmic membrane, the outer membrane or the intracytoplasmic membrane, or the membrane targeting sequence may target the protein to membranes nonspecifically. In preferred embodiments, the membrane targeting sequence targets the polypeptide, specifically or non-specifically to an intracytoplasmic membrane. Optionally, the membrane-targeting sequence is a membrane-targeting leader sequence positioned 5' relative to the expressible nucleic acid. In certain embodiments the membrane-targeting leader sequence is a leader sequence for a particulate methane monooxygenase subunit. In certain embodiments the leader sequence comprises a nucleic acid sequence encoding an amino acid sequence selected from the group consisting of: SEQ ID NO: 3, SEQ ID NO: 9, SEQ ID NO:10 and functional variants thereof, or a nucleic acid sequence selected from the group consisting of: SEQ ID NO: 5 and functional variants thereof. In some embodiments, the expression construct comprises a transcriptional terminator sequence operably linked to the expressible nucleic acid, and optionally the transcriptional terminator comprises a nucleic acid sequence selected from the group consisting of: SEQ ID NO:6, SEQ ID NO:8 and functional variants thereof.

In certain embodiments, the invention relates to vectors comprising an expression construct of the invention. A vector may be, for example, an autonomously replicating vector or an integrative vector. A vector may also be, for example, a viral vector, an autonomously replicating plasmid, an integrative or suicide plasmid, a transposon or a combination thereof. A vector may also comprise sequences that assist in replication or selection of the vector, such as an origin of replication and an antibiotic resistance cassette.

In additional embodiments, the invention relates to cell comprising an expression construct of the invention. The expression construct may be present in the cell in the context of an episomal nucleic acid, as in the case of many autonomously replicating vectors. The expression construct may also be present in the cell in the context of a vector integrated into the genome of the cell, or the expression construct may be integrated into the genome with no other vector sequences. In certain embodiments, the cell is selected for compatibility with the promoter of the expression construct. For example, the cell may be selected such that the promoter is endogenous to the cell. The cell may be a bacterium, such as a bacterium having an intracytoplasmic membrane system, for expression of the expression construct. A bacterium may also be another bacterial species, such as *Escherichia coli* (*E. coli*) or *Bacillus subtilis* that is useful for maintaining or propagating the expression construct. An expression construct may be inserted into a eukaryotic cell as well.

In further embodiments, the invention relates to cloning vectors comprising a membrane targeting sequence, a promoter for expression of a nucleic acid in a bacterial cell having an intracytoplasmic membrane system and a cloning site, the cloning site positioned such that an expressible nucleic acid inserted at the cloning site is operably linked to the promoter and the membrane targeting sequence. Optionally, the cloning vector further comprises a transcriptional terminator sequence positioned such that an expressible nucleic acid inserted at the cloning site is operably linked to the transcriptional terminator sequence. A cloning site may any site that facilitates the insertion of an expressible nucleic acid into the cloning vector. Exemplary cloning sites include: a restriction site, a topoisomerase recombination site, a recombinase recombination site and a transposase recognition site. The vector may also include a series of cloning sites together, forming a multiple cloning site, such as a polylinker. A cloning vector may be, for example, a viral vector, a broad host range plasmid, an *E. coli*-specific cloning vector or a hybrid plasmid/phage vector such as a phagemid. In certain embodiments the cloning vector includes a pmo promoter, such as a promoter comprising a sequence of SEQ ID NO:1, SEQ ID NO:2, SEQ ID NO:4 and SEQ ID NO:7, or a functional equivalent thereof, or a viral promoter. In certain embodiments the cloning vector includes a membrane targeting sequence that is a leader sequence, such as a nucleic acid sequence encoding an amino acid sequence selected from the group consisting of: SEQ ID NO:3 and functional variants thereof.

In yet additional embodiments, the invention relates to a cell comprising the cloning vector of the invention. Exemplary cell types include methanotrophs, nitrifying bacteria and common cloning bacteria such as *E. coli*.

In further embodiments, the invention relates to methods of cloning an expressible nucleic acid to form an expression construct. For example a method may comprise forming a mixture comprising a cloning vector of claim 24 and an insert comprising the expressible nucleic acid to be cloned and causing insertion of the insert at the cloning site of the cloning vector, thereby generating a vector comprising an expression construct. Methods may further comprise transforming a competent cell with the vector. Certain embodiments of the invention further relate to methods for making an expression product in a cell having an intracytoplasmic membrane system, such as a methanotroph or a nitrifying bacterium. Optionally, the expression product is a nucleic acid or a polypeptide. In certain embodiments, the invention relates to a method for producing a membrane protein, the method comprising culturing a methanotroph cell comprising an expression construct that comprises an expressible nucleic acid encoding a membrane protein that is foreign to the methanotroph cell under conditions suitable for production of the membrane protein, thereby producing a membrane protein. Optionally the expression construct further comprises a membrane targeting sequence operably linked to the expressible nucleic acid, and a promoter suitable for expression of the expressible nucleic acid in the cell. Optionally, culturing the cell under conditions suitable for production of the polypeptide comprises exposing the cell to copper(II), provided, for example, at a concentration ranging from about 5 µM to about 50 µM. In certain embodiments, methods further comprise preparing a partially purified or purified polypeptide. Methods may also include downstream use of prepared proteins for, for example, therapeutic, industrial or research purposes.

In yet additional embodiments, the invention relates to kits comprising a cloning vector of the invention and an additional component. Additional components may include a cloning enzyme, an enzyme buffer, competent cells, an oligonucleotide and instructions. Examples of cloning enzymes are ligases, recombinases, transposases, topoisomerases and restriction enzymes. Oligonucleotides may be designed for amplification of a portion of the vector by PCR (or another amplification technique) and may, for example, be designed to amplify across the portion of the cloning vector where an expressible nucleic acid would be inserted.

The embodiments and practices of the present invention, other embodiments, and their features and characteristics, will be apparent from the description, figures and claims that follow, with all of the claims hereby being incorporated by this reference into this Summary.

BRIEF DESCRIPTION OF THE DRAWINGS

FIG. 1 is an electron micrograph of a methanotroph, *Methylomonas methanica* (*M. methanica*), illustrating the intracytoplasmic membrane structures.

FIG. 2 is a schematic of an exemplary expression construct of the invention that is suitable for expression of an integral membrane protein in a methonotrophic bacterium.

FIG. 3 is a schematic of an exemplary minitransposon expression construct.

FIG. 4 shows the complete 5'-upstream sequence of the pmoC1 locus containing the pmo1 promoter of *Methylococcus capsulatus* Bath. The bold, italicized "a" indicates the transcriptional start site, and the underlined sequence indicates the promoter and regulatory sequences.

FIG. 5A shows exemplary membrane targeting leader sequences (nucleic acid and amino acid) from the pmoC1 gene of *M. capsulatus* Bath. A signal peptidase cleavage site is in the amino acid sequence AAAAEA; cleavage occurs between the third and fourth alanine residues (i.e. AAA/AEA).

FIG. 5B shows an exemplary membrane targeting leader sequence from Flavobacterium.

FIG. 6 shows an exemplary transcriptional terminator sequence, the 3'-flanking region of the pmo1 locus containing the pmo1 transcriptional terminator.

FIG. 7 shows sequence of the 5'-upstream of the pmoC2 containing the pmo2 promoter. The bold, italicized "a" indicates the transcriptional start site, and the underlined sequence indicates the promoter and regulatory sequences.

FIG. 8 shows an exemplary transcriptional terminator sequence, the 3'-flanking region of the pmo2 locus containing the pmo2 transcriptional terminator sequence.

DETAILED DESCRIPTION

1. Definitions:

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

A "cell having an intracytoplasmic membrane system" is intended to refer to bacteria having membrane structures in the cytoplasm, or internal to the cytoplasmic membrane that forms the boundary between the cytoplasm and the extracellular space (or periplasm). An intracytoplasmic membrane system may be separate from or connected to the cytoplasmic membrane or another membrane system.

A "chimeric polypeptide" or "fusion polypeptide" is a fusion of a first amino acid sequence with a second amino acid sequence where the first and second amino acid sequences are not naturally present in a single polypeptide chain.

"To clone", as will be apparent to skilled artisan, may mean obtaining exact copies of a given polynucleotide molecule using recombinant DNA technology. Details of molecular cloning can be found in a number of commonly used laboratory protocol books such as Molecular Cloning: A Laboratory Manual, 2nd Ed., ed. by Sambrook, Fritsch and Maniatis (Cold Spring Harbor Laboratory Press: 1989).

"To clone", as will be apparent to skilled artisan, may also mean obtaining identical or nearly identical population of cells possessing a common given property, such as the presence or absence of a fluorescent marker, or a positive or negative selectable marker. The population of identical or nearly identical cells obtained by cloning is also called a "clone." Cell cloning methods are well known in the art as described in many commonly available laboratory manauls (see Current Protocols in Cell Biology, CD-ROM Edition, ed. by Juan S. Bonifacino, Jennifer Lippincott-Schwartz, Joe B. Harford, and Kenneth M. Yamada, John Wiley & Sons, 1999).

A "cloning site" is any nucleic acid sequence that facilitates the combination of a vector and an insert, for the purpose of cloning the insert. A cloning site may be, for example, a restriction site, a recombinase site, a topoisomerase site or a transposase site.

A "cloning vector" is a vector that has at least one cloning site positioned in such a way as to facilitate the construction of a recombinant nucleic acid or expression construct disclosed herein. A cloning vector may have many additional properties and functionalities. For example, a cloning vector may be an autonomously replicating vector or an integration vector.

The term "derived from" as used herein in reference to a nucleic acid means that at least a portion of the nucleic acid (e.g. gene, gene portion, regulatory element, polypeptide) is also present in (i.e. or was copied from) the biological source that the nucleic acid was derived from. The derived nucleic acid may be constructed in any way that provides the desired sequence, including the derivative portion. For example, nucleic acid may be obtained directly from the biological source, using restriction enzymes or other tools of molecular biology, or by amplifying from the biological source (e.g. by polymerase chain reaction), or by a technique such as chemical synthesis. While in many instances a nucleic acid derived from a biological source is not directly obtained from the source, its sequence and/or characteristics are substantially the same as a portion of sequence from the biological source.

An "expression construct" is any recombinant nucleic acid that includes an expressible nucleic acid and regulatory elements sufficient to mediate expression in a suitable host cell. For example, an expression construct may contain a promoter or other RNA polymerase contact site, a transcription start site or a transcription termination sequence. An expression construct for production of a protein may contain a translation start site, such as an ATG codon, a ribosome binding site, such as a Shine-Dalgarno sequence, or a translation stop codon.

The term "fusion protein" refers to a protein or polypeptide that has an amino acid sequence having portions corresponding to amino acid sequences from two or more proteins. The sequences from two or more proteins may be full or partial (i.e., fragments) of the proteins. Fusion proteins may also have linking regions of amino acids between the portions corresponding to those of the proteins. Such fusion proteins may be prepared by recombinant methods, wherein the corresponding nucleic acids are joined through treatment with nucleases and ligases and incorporated into an expression vector. Preparation of fusion proteins is generally understood by those having ordinary skill in the art.

The term "heterologous" as used in describing a nucleic acid with respect to another nucleic acid means that the two nucleic acids are not normally operably linked to each other or do not naturally occur in adjacent positions.

The term "including" is used herein to mean, and is used interchangeably with, the phrase "including but not limited to".

"Kit" as used herein means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation. The individual components of the kit may or may not be from the same supplier, or manufacturer. A component can either be purchased as a part of the kit, or generated by user "in-house" according to the instruction of the kit.

A "membrane protein" includes any protein that is associated with a cell membrane. Membrane proteins may be associated with the membrane by, for example, a hydrophobic modification that inserts into the membrane, by interaction with a membrane component such, as a lipid or protein, or by virtue of an amino acid domain that is inserted in the membrane. Proteins having an amino acid domain that is inserted into the membrane are referred to as "integral membrane proteins". Many integral membrane proteins are "transmembrane proteins", meaning that a substantial protein domain is positioned on either side of the membrane, and many integral membrane proteins are "multipass membrane proteins", meaning that the protein is threaded through the membrane by virtue of two or more amino acid domains inserted into the membrane.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The phrase "operatively linked to a promoter" means that the promoter is capable of directing the expression of the associated coding region. Coding regions may also be operatively linked to other regulatory elements, such as enhancers.

The term "or" is used herein to mean, and is used interchangeably with, the term "and/or", unless context clearly indicates otherwise.

The term "percent identical" refers to sequence identity between two amino acid sequences or between two nucleotide sequences. Percent identity can be determined by comparing a position in each sequence which may be aligned for purposes of comparison. Expression as a percentage of identity refers to a function of the number of identical amino acids or nucleic acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The term "plasmid" as used herein includes any small (less than 50 kb) circular nucleic acid vector. A plasmid will generally be autonomously replicating in at least one host cell, such as an *E. coli* cell. A plasmid may also be autonomously replicating in a cell having an intracytoplasmic membrane system, such as a methanotroph. A plasmid may also be designed to be an integrative vector, such as a suicide vector, in a cell having an intracytoplasmic membrane system, such as a methanotroph.

The terms "polypeptide" and "protein" are used interchangeably herein.

The term "pmo promoter" refers generally to a promoter that comprises a transcriptional regulatory element derived from a methanotrophic bacterium, wherein the transcriptional regulatory element, in its native genomic context, regulates the transcription of a gene encoding a subunit of a particulate methane monooxygenase. Exemplary pmo promoters include promoters such as the pmo1 and pmo2 promoters of *Methanococcus capsulatus* Bath as well as promoters comprising the underlined sequences of the pmo1 and pmo2 promoters shown in FIGS. 4 and 7. Exemplary pmo promoters also include promoters comprising functional variants of any of the preceding nucleic acids.

The term "promoter" is used herein to refer to any nucleic acid that provides sufficient cis-acting nucleic acid regulatory elements to support the initiation of transcription of an operably linked nucleic acid in the appropriate conditions. Appropriate conditions may include the presence or activation of appropriate trans-acting factors, such as an RNA polymerase, a sigma factor and a transcription factor. Appropriate conditions may also include the absence or inactivation of negative regulatory factors, such as repressors. Appropriate conditions may further include chemical and physical conditions such as pH and temperature that are compatible with promoter function. Exemplary regulatory elements that may be part of a promoter include sigma factor binding sites (or other RNA polymerase binding sites), transcription factor binding sites, small molecule binding sites, repressor binding sites, etc. For example, many bacterial promoters include one or more binding sites for a sigma factor, and the binding sites are often situated at an appropriate distance along the DNA from each other. For example, the major "housekeeping" sigma factor of *E. coli*, termed $\sigma^{70}$, recognizes loosely conserved sequences that are situated at roughly ten bases upstream of the transcription start site (the −10 box) and roughly thirty-five bases upstream of the transcription start site (the −35 box). A promoter may be affected by one or more cis-acting or trans-acting element that is external to the promoter. Many promoters are "conditional" or "regulated" meaning that the degree to which the promoter supports the initiation of transcription is affected by one or more conditions inside or outside the cell.

A "polypeptide composition" is a composition comprising polypeptides. A polypeptide composition may also comprise other components such as salts, buffers, small molecules, detergents, lipids, etc. A "partially purified polypeptide composition" is a polypeptide composition produced after at least one step designed to enrich for a polypeptide of interest. For example, a membrane preparation obtained from a bacterial culture is a partially purified polypeptide composition with respect to a membrane protein because, with the removal of soluble proteins the composition will be enriched for a subject membrane protein. A "purified polypeptide composition" is a composition comprising polypeptides, wherein at least about 80% of the polypeptides are of a single species (or insubstantial variants of a single species, such as in the case of a polypeptide having slightly different post-translational modifications). A partially purified and purified polypeptide composition may comprise many other components such as salts, buffers, small molecules, detergents, lipids, etc.

A "regulatory element" or "regulatory sequence" is an amino acid or nucleic acid sequence that regulates a process relating to transcription, translation, post-translational modifications and processing, protein maturation or protein localization. Exemplary regulatory elements include transcription factor biding sites, membrane targeting sequences, translation initiation codons, ribosome binding sites (e.g. Shine-Dalgarno sequences), and transcription termination sequences.

The term "recombinant nucleic acid" includes any nucleic acid comprising at least two sequences which are not present together in nature. A recombinant nucleic acid may be generated in vitro, for example by using the methods of molecular biology, or in vivo, for example by insertion of a nucleic acid at a novel chromosomal location by homologous or non-homologous recombination.

The term "vector" refers to a nucleic acid molecule capable of transporting another nucleic acid to which it has been linked. One type of vector is an episome, i.e., a nucleic acid capable of extra-chromosomal replication. Another type of vector is an integrative vector that is designed to recombine with the genetic material of a host cell. Vectors may be both autonomously replicating and integrative, and the properties of a vector may differ depending on the cellular context (i.e. a vector may be autonomously replicating in one host cell type and purely integrative in another host cell type). Vectors capable of directing the expression of genes to which they are operatively linked are referred to herein as "expression vectors".

2. Methods for Expressing Nucleic Acids and Polypeptides:

In certain embodiments, the present invention makes use of bacterial cells having an intracytoplasmic membrane system for use in methods for the expression and production of proteins, and particularly membrane proteins. In certain embodiments, the invention relates to a method for expressing a nucleic acid or polypeptide, the method comprising culturing a cell having an intracytoplasmic membrane system, where the cell comprises an expression construct comprising a promoter operably linked to an expressible nucleic acid, thereby achieving expression of the expressible nucleic acid. Optionally the expressible nucleic acid is foreign to the cell. Optionally the expressible nucleic acid encodes a polypeptide, and in preferred embodiments, the polypeptide is a membrane protein, such as an integral membrane protein or a multipass membrane protein. In certain preferred embodiments, the recombinant nucleic acid construct includes a membrane-targeting leader sequence that targets at least a portion of the expressed protein to a membrane, such as the plasma membrane or an intracytoplasmic membrane. Optionally, the expression construct may comprise a transcriptional terminator that is operably linked to the expressible nucleic acid.

In certain embodiments, the use of a cell having an intracytoplasmic membrane system for the production of membrane proteins provides higher yields of membrane protein than are obtained with a conventional expression cell type, such as an *E. coli* expression system, a methylotrophic yeast system or a baculovirus system. While not wishing to be bound by theory, it is expected that the high yields of membrane protein obtained in this manner are partly due to the increased membrane area in which membrane proteins may accumulate. While preferred embodiments of the invention involve the expression of membrane proteins, methods described herein may also be useful for the expression of soluble (or insoluble non-membrane proteins) or secreted proteins and for the expression of nucleic acids that do not encode proteins. Cells having an intracytoplasmic membrane system may, in certain embodiments, provide other advantages for the production of proteins and nucleic acids generally. For example, many proteins are toxic in cells that are commonly used for protein production, such as *Escherichia coli* and *Bacillus subtilis*, making cloning and expression difficult or impossible. Cells having intracytoplasmic membrane structures may provide a useful alternative expression system. A number of bacteria have intracytoplasmic membrane systems, and in certain bacteria the intracytoplasmic membrane system is developed to the point that the internal membrane surface is many times greater than the membrane surface of the cytoplasmic membrane. In many instances, a cell having an intracytoplasmic membrane system does not have such a system in all growth conditions, but only in certain growth conditions, and the use of cells having this type of conditional intracytoplasmic membrane system, as well as cells having constitutive (or permanent) intracytoplasmic membrane systems is specifically included in certain embodiments of the invention. Optionally, cells for use in the expression of nucleic acids and proteins are cells having an intracytoplasmic membrane system that provides a membrane surface area that is at least equivalent to the surface area of the cytoplasmic membrane, and optionally the cells have an intracytoplasmic membrane system that has at least several times greater surface area than the surface area of the cytoplasmic membrane. Preferably, the cells have an intracytoplasmic membrane system that has about 20-100 times greater surface area that the surface area of the cytoplasmic membrane. Exemplary cells having intracytoplasmic membrane systems are methanotrophs and ammonia oxidizing bacteria.

Methanotrophs are Gram-negative bacteria that are able to use many C1 compounds (methane, methanol, methyl formate, formaldehyde) as sole energy and carbon sources. They are able to use nitrate, ammonia and ammonium salts as nitrogen sources. During growth on methane, and to a lesser extent methanol, these organisms express a methane monooxygenase enzyme to catalyze the conversion of methane to methanol. Exemplary methanotrophs include type I methanotrophs of the γ-Proteobacteria, such as members of the genus Methylococcus, and type II methanotrophs of the α-Proteobacteria, such as members of the genera Methylocystis and Methylosinus. In many methanotroph strains, two parallel methane monooxygenase systems exist, a soluble methane monooxygenase and a particulate methane monooxygenase. In certain methanotrophs, such as *Methylococcus capsulatus* Bath, the soluble methane monooxygenase (sMMO) is expressed in copper limitation conditions, and when copper is not limiting (e.g. at copper concentrations >0.2 μM), these bacteria synthesize an integral membrane protein containing copper, the particulate methane monooxygenase (pMMO). The transcriptional switch is regulated by Cu(II) ions. To maintain robust growth, these organisms synthesize a vast amount of pMMO. For instance, in *Methylococcus capsulatus* Bath the particulate methane monooxygenase constitutes >30%-50% of total cellular proteins despite the fact that it is a membrane protein. Furthermore, as a consequence of pMMO overexpression, certain methanotrophs synthesize and accommodate an extensive network of intracytoplasmic membranes which constitute an internal membrane surface of ~20-100 times greater than the cell surface alone, a feature not known to exist in other organisms presently used for expression of nucleic acids and proteins.

Further exemplary methanotrophs are *Methylosinus sporium*, *Methylocytis parvus* and other species of the genera Methylomonas and Methylobacter. A variety of methanotrophs, deposited in the Agriculture Research Service Culture Collection (NRRL) 1815 North University Street, Peoria, Ill. 61604, are listed in U.S. Pat. No. 4,269,940. Further methanotrophs are available at the American Type Culture Collection (ATCC) 10801 University Boulevard, Manassas, Va. 20110, and examples of these are shown in Table 1.

TABLE 1

Exemplary Methanotrophs in the ATCC

| ATCC Number | Description |
|---|---|
| 14821 | *Methylobacterium rhodinum* (Heumann) Green and Bousfield deposited as *Pseudomonas rhodos* Heumann |
| 19069 | *Methylococcus capsulatus* Foster and Davis |
| 20563 | *Methylomonas probus* |
| 21369 | *Methanomonas methylovora* Kono et al. |
| 21370 | *Methanomonas methylovora* subsp. *Thiaminophila* Kono et al. |
| 21371 | *Methylobacterium* sp. deposited as *Protaminobacter thiaminophagus* |
| 2372 | *Methylobacterium* sp. deposited as *Protaminobacter candidus* |
| 33003 | *Methylomicrobium album* (Whittenbury et al.) Bowman et al. deposited as *Methylomonas albus* Whittenbury et al. |
| 33009 | *Methylococcus capsulatus* Foster and Davis |
| 35068 | *Methylomicrobium agile* (Bowman et al.) Bowman et al. deposited as *Methylomonas agile* Whittenbury et al. |
| 35069 | *Methylomicrobium sporium* (ex Romanovskaya et al.) Bowman et al. |
| 49878 | *Methylobacter luteus* (Romanovskaya et al.) Bowman et al. |
| 51738 | *Methylobacter whittenburyi* (Romanovskaya et al.) Bowman et al. |
| 49242 | *Methylosinus trichosporium* Bowman et al. |
| 49243 | *Methylosinus trichosporium* Bowman et al. |

Further exemplary methanotrophs include: *Methylosinus trichosporium*, *Methylomonas methanica*, *Methylomonas*

*albus, Methylomonas streptobacterium, Methylomonas agile, Methylomonas rubrum, Methylomonas rosaceus, Methylobacter chroococcum, Methylobacter bovis, Methylobacter vinelandii,* and *Methylococcus minimus.*

*Methylosinus trichosporium* OB3b is a further exemplary methanotroph. It is an obligate type II methanotrophic bacterium which is capable of growing on methane as its sole source of carbon and energy. This bacterium was discovered by Whittenbury et al., J. Gen. Microbiol., 61:205-218 (1970). Strains of this bacterium are deposited with the National Collection of Industrial, Marine and Food Bacteria, Aberdeen, Scotland and assigned number NC1B-11131.

Ammonia oxidizing bacteria, also know as nitrifying bacteria, express a protein called ammonia monooxygenase that has many characteristics in common with the particulate methane monooxygenase, including localization to an extensive intracytoplasmic membrane system. Accordingly, ammonia oxidizing bacteria are suitable for use in certain embodiments of the invention. Nitrifying bacteria are Gram negative, obligate aerobic chemolithotrophs which oxidize ammonium to nitrite or nitrite to nitrate as their sole energy source and assimilate carbon dioxide via the Calvin Benson cycle. One group of nitrifying bacteria is in the γ-Proteobacteria subclass and the other group is in the β-Proteobacteria. Exemplary ammonia oxidizing bacteria include members of the genus Nitrosomonas, such as *Nitrosomonas europaea*, members of the genus Nitrosococcus, such as *Nitrosococcus mobilis*, and members of the genus Nitrosospira, such as *Nitrosospira briensis*.

Recombinant nucleic acids of the invention may be introduced into host cells in a variety of ways known in the art. For example, methanotrophs may be transformed with broad host range vectors by a conjugation technique (biparental or triparental mating, depending on the nature of the vectors, self-replicating, suicidal, or genome integrative proficient). Basically, a methanotroph and an *E. coli* helper strain, such as S17-1, that the vector(s), are incubated together as described by Stoylar et al, M. E. (2001) *J. Bact.* 183, 1810-1812.; Lloyd, J. S., Finch, R., Dalton, H., Murrell, J. C. (1999) *Microbiology* 145, 461-470. b) Lloyd, J. S., De Marco, P., Dalton, H., Murrell, J. C. (1999) *Arch. Microbiol.* 171, 364-370; Chistoserdov, A. Y. et als. (1994) *J. Bacteriol.* 176, 4052-4065. After approximately 48 hr, the bacteria are collected and plated onto NMS medium agar plates containing the selection marker(s). The NMS medium for methanotroph isolation contains only essential nutrients and is partially selective for methanotrophs. The inclusion of a selectable marker, such as antibiotic resistance cassette or a chromogenic or fluorogenic gene, and the use of corresponding selection conditions, will allow only clones containing the desired construct to grow. In the case of self-replicating expression vectors, electroporation, may be used, as may simple methods ($CaCl_2$ or $LiCl_2$ washing) to prepare competent cells for transformation by heat shock.

Culture conditions will generally be selected as is appropriate for the cell type. If particular conditions are required for the cell to produce an intracytoplasmic membrane system, it may be desirable to expose the cells to those conditions. For example, many methanotrophs, including *M. capsulatus* Bath, generate an internal membrane structure in response to copper, and particularly copper(II) ions. In an embodiment of the invention, a methanotroph containing an expression construct of the invention is cultured in the presence of copper(II) ions (supplied, for example, as a salt with an anion that is biologically compatible and soluble, such as $CuCl_2$ or $CuSO_4$) at a concentration greater than about 0.2 µM, optionally greater than about 5 µM and preferably in a range between about 5 µM and 50 µM. Preferably copper is supplied in a form and at a concentration low enough to avoid toxic effects.

In certain embodiments, expression of the nucleic acid or polypeptide may be inducible. For example, certain pmo promoters are more active when the cell is exposed to copper(II) ions and less active in low copper concentrations, particularly if ample iron is supplied. As another example, the well-known *E. coli* lac promoter is induced by isothiopyranogalactose (IPTG). In embodiments where expression of a nucleic acid or polypeptide is inducible, it may be desirable to culture the cells to a certain density or growth stage in the absence of the inducing condition, and then shift the cells to the inducing condition. For example, cells may be shifted to inducing conditions at or near the beginning of the exponential growth phase, at or near the mid-point of the exponential growth phase, or at or near the transition from the exponential growth phase to the stationary growth phase. These phases of culture growth generally occur in simple cultures where the effects of the bacteria on the culture (e.g. changes in pH, exhaustion of nutrients, buildup of harmful waste products) are not compensated for. In some complex culture systems, such as chemostats, culture conditions are monitored and manipulated so as to maintain a steady-state cell density and growth rate, or to achieve other cell culture kinetics that are difficult to achieve with simple cultures. In the case of such complex culture systems, the appropriate time of induction may be determined on the basis of cell density, culture growth rate or another relevant characteristic. In certain embodiments, cells are exposed to inducing conditions at approximately the same time that cells are exposed to conditions that stimulate production of the intracytoplasmic membrane system.

As an example of culture conditions, methanotrophs may be grown on nitrate mineral salts medium (NMS) (Whittenbury et al., 1970, J. Gen. Microbiol. 61:205-18) in batch culture with a headspace of methane and air (1:5) at 30° C. or on NMS agar plats under the same conditions. As a further example of growth conditions, methanotrophs may be grown on nitrate mineral salts medium in batch culture with copper added as $CuSO_4\text{-}5H_2O$. For *Methylobacter marinus* A45 (or other marine species) a sterile solution of NaCl may be added for a final concentration of 1% (wt/vol). The cells may be shaken at 200 rpm under a methane-air headspace (approximately 1:3 vol/vol) at 1 atm (101.29 kPa) of pressure. *Methylobacter albus* BG8 (previously called *Methylomonas albus* BG8), *Methylocystis parvus* OBBP, and *Methylosinus trichosporium* OB3b are optionally grown at 30° C., while *Methylococcus capsulatus* Bath is preferably grown at 45° C. and *Methylbacter marinus* A45 is preferably grown at 37° C. These exemplary culture conditions may be adjusted as desired by one of skill in the art.

In certain embodiments, methods of the invention comprise obtaining purified or partially purified preparations of a product produced in a cell of the invention. An product may be, for example, an expression product such as an RNA or a polypeptide, or a product such as a plasmid, a phage particle or a genomic DNA preparation. In general, except in the case of certain secreted proteins, protein purification comprises a step of cell lysis. Cell lysis may be achieved in a variety of ways, including sonication, French press (or other shearing methods), repeated freeze-thawing, or treatment with a membrane disrupting agent, such as detergent, particularly an anionic detergent such as sodium dodecyl sulfate in the presence of strong base. Note that certain methods of lysis cause protein denaturation and are suitable if the native protein is not the desired product. After cell lysis the cell debris may be removed by centrifugation and a partially purified polypeptide composition may be obtained by separating the membrane fraction from the soluble fraction by a high-speed centrifugation (e.g. a centrifugation that generates forces in excess of 50,000×g). If the desired protein is a soluble protein, the membrane fraction (pellet) may be discarded, and if the desired protein is a membrane protein, the soluble fraction may be discarded. Soluble and insoluble fractions may also be separated by other methods such as filtration. Further purification steps may be employed as desired. For example, membrane proteins may be solublized by, for example, sonication or detergent treatment. Further purification steps may include affinity purification, anion or cation exchange chromatography, reverse phase chromatography, hydrophobic interaction chromatography, isoelectric focusing, size fractionation, etc. In certain preferred embodiments a protein of interest is expressed as a fusion protein with an affinity purification tag that facilitates rapid enrichment in a single affinity purification step. Exemplary affinity purification tags include histidine tags (e.g. hexahistidine tags, purified on nickel, copper or other metal resins), glutathione-S-transferase tags (purified on a glutathione resin), cellulose binding protein tags (purified on cellulose), and many others known in the art. Optionally a protease cleavage site is incorporated to allow separation of the affinity purification tag from the protein of interest. In most instances, an affinity purification tag may be incorporated at the amino- or carboxy-terminus of a protein.

Purification of chromosomal DNA from a cell having an intracytoplasmic membrane system may be performed by, for example, a standard phenol extraction/isopropanol precipitation protocol as described, for example, in Semrau et al., 1995, J. Bacteriol. 177:3071-79. Purification of plasmid DNA may be achieved by, for example, following a sodium dodecylsulfate lysis/isopropanol precipitation procedure as described in Semrau et al. Many other techniques for purifying genomic and plasmid DNA are known in the art.

Purified and partially purified polypeptide compositions may be used in a variety of applications ranging from research to commercial and therapeutic applications. For example, polypeptides may be characterized biochemically (e.g. activity assays) or structurally (e.g. x-ray crystallography, nuclear magnetic resonance, mass spectroscopy). As a further example, a purified polypeptide may be used in an industrial process. For example, a variety of degradative enzymes such as pectinases, cellulases, and hydrolyases are used industrially. Purified polypeptides may also be prepared as a therapeutic composition for administration to a human or other subject.

3. Recombinant Nucleic Acids and Expression Constructs

In certain embodiments, the present invention relates to recombinant nucleic acids that comprise an expressible nucleic acid (a nucleic acid to be expressed in a cell having an intracytoplasmic membrane system) and regulatory sequences that function for use in expressing the expressible nucleic acid in a cell having an intracytoplasmic membrane system and are positioned in the recombinant nucleic acid such that expression, and optionally a post-transcriptional processing event, of the expressible nucleic acid sequence is under control of the regulatory sequences. Regulatory sequences may influence processing events such as translation, post-translational modification, protein targeting (e.g. to a membrane) or transcript or protein degradation. In some aspects, the invention relates to recombinant nucleic acids comprising a promoter or membrane targeting sequence operably linked to the expressible nucleic acid. In certain embodiments, the recombinant nucleic acid comprises a transcriptional terminator sequence, also operably linked to the expressible nucleic acid. In further embodiments, the invention relates to expression constructs comprising a membrane targeting sequence operably linked to an expressible nucleic acid and a promoter suitable for expression of the expressible nucleic acid in a cell. In additional embodiments, the promoter is designed to cause constitutive or conditional expression of an operably linked nucleic acid in a cell having an intracytoplasmic membrane system. In certain embodiments, the expressible nucleic acid is heterologous with respect to one or more of the regulatory sequences, meaning that it is not normally, in nature, operably linked to the respective regulatory sequence. Optionally, the expressible nucleic acid is not endogenous to the cell in which it is to be expressed.

In certain embodiments, a promoter for use in a recombinant nucleic acid of the invention is a pmo promoter. A pmo promoter is a promoter that comprises a transcriptional regulatory element derived from a gene encoding a polypeptide of a particulate methane monooxygenase. For example, a pmo promoter of the invention may be obtained by cloning, synthesizing, amplifying or otherwise obtaining a portion of the nucleic acid sequence that is upstream of a gene encoding a particulate methane monooxygenase gene. A pmo promoter may comprise a complete promoter from a pmo gene or a core promoter from a pmo gene. A pmo promoter may also be chimeric, with portions of the promoter obtained from different sources. For example, a pmo promoter may comprise a −10 region, −35 region or other transcription factor binding site from upstream of a pmo gene. An exemplary chimeric pmo promoter comprises a strong, constitutive core promoter from a virus and a copper-responsive regulatory region derived from a pmo gene. Exemplary pmo promoters include promoters comprising one or more of the following nucleic acid sequences from the *Methylococcus capsulatus* Bath pmo1 or pmo2 promoters:

5'-ccctgcgtcaaaatgtcgca-gatttttcttgacagtttggggagggtgatagatc-3' (SEQ ID NO:1)

5'-cctgcg tcaaaatgacgcagatttttcctga-cagcctcgggttgggtgatagact-3' (SEQ ID NO:2)

Exemplary pmo promoters also include promoters comprising functional variants of any of the preceding nucleic acid sequences. Pmo promoters may be obtained using conventional techniques of molecular biology. For example, a probe generated from a known pmo sequence of *M. capsulatus* Bath may be used to identify and isolate pmo sequences from a different methanotroph. Exemplary methods for obtaining pmo sequences from several different methanotrophs are described in Gilbert et al., 2000, Appl. Eviron. Microbiol. 66:966-75. Exemplary pmo promoters also include promoters comprising the sequences shown in FIGS. 4 and 7 and functional variants thereof. Functional variants of any of SEQ ID Nos: 1, 2, 4 or 7 include sequences that are at least 80% identical to the corresponding, SEQ ID NO., and optionally at least 90%, 95%, or at least 99% identical to the corresponding SEQ ID NO.

In further embodiments, the promoter may be a viral promoter such as a promoter from a bacteriophage. For example, many lytic double-stranded DNA bacteriophages capable of replicating in methanotrophs have been described (Tyutikov et al., 1980, J. Bacteriol. 144:375-81; Tyutikov et al., 1983, Appl. Environ. Microbiol. 46: 917-24). A phage strain that lyses a methanotroph, such as *Methylocystis* sp. or *M. trichosporium* may be used as a source of a phage promoter. In particular, promoters for viral coat proteins are strong promoters.

For example, a methanotroph phage promoter may be obtained according to the following exemplary method: a phage capable of lysing a laboratory strain of *Methylocystis* sp. or *M. trichosporium* is selected. Upon obtaining high titer preparations, phage particles are purified by ethylene glycol precipitation followed by cesium chloride banding. Viral DNA is obtained by lysing phage preparations in SDS, digested with proteinase K to remove viral proteins, followed by phenol-chloroform extraction and ethanol precipitation. The purified viral DNA is fragmented with specific restriction enzymes and cloned into pBR322 vector. The nucleotide sequence is determined using widely available high-throughput sequencing techniques. The genome size of these phages is generally about 30 megadaltons (~-60 kb), hence very manageable. The sequence information is used to map the virus genetic organization, and to identify cis-elements essential for viral replication and expression of abundant viral proteins such as coat proteins. Candidate promoters may be tested in a reporter gene assay or other promoter functionality test as described below. Further exemplary steps may be taken to identify viral promoters: SDS-PAGE analysis of the viral particles may be performed to determine the size and abundance of individual viral coat protein subunits and their N-terminal sequences may be obtained by protein blotting and Edman degradation sequencing. The 5' fragment upstream of the viral coat proteins sequence may be cloned into a broad host range plasmid for the following exemplary promoter functionality test. A competent permissive corresponding methanotroph strain is be transformed with a broad host range plasmid containing the putative promoter sequence fused with a reporter gene (e.g. β-galactosidase) and individual clones are selected using specific antibiotics on the plasmid. These clones are infected with the lytic bacteriophage and the lysate from the infected cells is examined for the expression of the β-galactosidase.

Promoters, such as pmo promoters and viral promoters, may be altered to generate variants. A wide range of art-recognized techniques are available for generating variants of promoters. Exemplary techniques include oligonucleotide-based site directed mutagenesis, propagation of a plasmid in an error-prone *E. coli* strain, restriction digestion and re-ligation after digestion with an exonuclease to create deletions or re-ligation with an insert to create insertions, etc. The functionality of a variant may be assessed by generating a construct that operably links the variant promoter to a reporter gene. A reporter gene will generally be selected for effectiveness in a host cell. For example, if it is desirable to assess the functionality of a promoter variant in a methanotroph, the reporter gene should be one that functions in a methanotroph. An exemplary reporter gene for methanotrophs is the xylE gene that encodes a catechol dioxygenase. Exemplary reporter gene assays are described in Stolyar et al. (2001) J. Bacteriol. 183: 1810-12 and Kataeva and Golovleva (1990) Methods Enzymol. 188:115-21. In certain instances a fluorogenic reporter gene may be used. Exemplary fluorogenic reporter genes include luciferase, green fluorescent proteins (and the colored variants thereof), and enzymes for which fluorogenic substrates are available, such as beta-galactosidase. Fluorogenic reporter genes are particularly amenable to high-throughput methods. In an exemplary high-throughput method, a large number of promoter variants are generated, cloned into a fluorogenic reporter gene construct and transformed into host cells. A large number of transformants are selected and cultured in 96 well plates under conditions in which the promoter should be active, and a fluorescent readout is obtained for each transformant. Functionality of a promoter may also be assessed by measuring levels of mRNA produced from the promoter. For example, oligomers specific for the sequence of the mRNA of interest may be used for quantitative RT-PCR to measure production of the mRNA expressed from the promoter variant. In certain instances, a variation in a promoter will cause a change in the transcription start site. The transcription start site may be assessed by performing the well-known technique of primer extension. An exemplary primer extension assay is described in Stolyar et al., supra. In view of this specification, other methods for assessing promoter functionality will be apparent to those of skill in the art.

While the tools of molecular biology make it possible to assess the functionality of a large number of randomly or semi-randomly generated promoter variants, there are many instances where changes in promoters will have relatively predictable effects. For example, typical bacterial promoters comprise two regulatory elements that provide contact sites for the sigma factor (a subunit of RNA polymerase). In the case of the primary "housekeeping" sigma factor of the γ-Proteobacteria, known as (σ70, there is a sigma factor contact point positioned at or near the −35 position relative to the transcription start site and a second contact point positioned at −10. Displacing these sequences relative to each other (i.e. increasing or decreasing the number of nucleotides between these sequence elements) or relative to the transcription start site (e.g. shifting the sequence elements to the −40 and −15 positions) will generally cause a decrease in transcription initiation by the promoter, with displacements larger than two or three nucleotides causing near-complete or complete elimination of promoter function. The exact sequence of nucleic acids between the −35 and −10 sequences is generally less important than the spacing, unless an additional regulatory sequence is positioned there. Most bacteria have several sigma factors, and each sigma factor has a set of corresponding contact point sequences and spacings that are compatible with promoter function. Accordingly, an understanding of the principles of bacterial promoter design and function permits rational generation of variants with an increased likelihood of having the desired functional attributes.

A promoter may be considered operably linked to a nucleic acid if the promoter and the nucleic acid are positioned such that the nucleic acid is transcribed when the expression construct is placed in appropriate conditions (e.g. the correct cell type, in the presence of necessary inducers or in the absence of active repressors).

A membrane targeting sequence, in the context of a nucleic acid, is a nucleic acid sequence that encodes an amino acid sequence that, when expressed as part of a polypeptide (e.g. a fusion protein), causes the expressed polypeptide to be targeted to a membrane. In the context of a polypeptide, a membrane targeting sequence is a sequence of amino acids that causes the polypeptide to be targeted to a membrane. In certain embodiments, a membrane targeting sequence is a leader sequence, meaning that it is positioned so as to be expressed at or near the beginning of a polypeptide. In certain embodiments, a membrane targeting sequence may also be positioned at or near the end of a polypeptide, or positioned in the interior. It is also contemplated that a membrane targeting sequence may be a dispersed set of sequences distributed in non-consecutive positions in a polypeptide or nucleic acid.

Membrane targeting may be a complex process, depending on the complexity of the membrane organization in a cell. Methanotrophs and ammonia oxidizing bacteria generally have at least two membrane systems that may be distinguished ultrastructurally: a membrane that forms a boundary between the cytoplasm and the periplasm (or extracellular space in bacteria that lack an outer membrane), termed the "cytoplasmic membrane" and a membrane that resides within the cytoplasm, termed the "intracytoplasmic membrane".

Many bacteria, including methanotrophs and ammonia oxidizing bacteria, have an "outer membrane" that forms the boundary between the periplasm and the extracellular space. Targeting to a particular membrane structure may involve one or more membrane targeting domains. Certain membrane targeting sequences will specifically target polypeptides to a single membrane system, while other non-specific membrane targeting sequences will target polypeptides to more than one membrane system. In certain preferred embodiments, a membrane targeting sequence of the invention targets an expressed polypeptide to an intracytoplasmic membrane system specifically or non-specifically. Membrane targeting sequences may be naturally cleaved off of the targeted polypeptide during the targeting process, or the targeting domain may remain attached. In certain embodiments, the expression construct may be engineered to provide a cleavage site between the targeting domain and the polypeptide. The cleavage site may be recognized by a protease in vivo or by a protease that is supplied after the protein has been at least partially purified. Exemplary proteases to be supplied after partial purification include: factor Xa, enterokinase and thrombin.

Exemplary membrane targeting sequences include the leader sequences of any of the various pmo genes, and particularly the leader sequences for pmoC genes. Membrane targeting sequences may also be taken from other membrane proteins in cells having an intracytoplasmic membrane system and even in cells not having an intracytoplasmic membrane systems. Often membrane targeting sequences from one bacterial species are effective in a wide range of taxonomically diverse bacteria. For example, a leader sequence from a Flavobacterium membrane protein, such as organophosphorous hydrolyase is effective for membrane targeting in *Methylococcus capsulatus* Bath, and accordingly, an exemplary membrane targeting sequence is a nucleic acid encoding the following amino acid sequence:

Am- MQTRRVVLKSAAAGTLLGGLAGCASVAG-Ac (SEQ ID NO:9) and functional variants thereof.

Exemplary membrane targeting sequences include nucleic acids encoding the following amino acid sequences from the *Methylococcus capsulatus* Bath pmoC1 gene:

Am-MAATTIGGAAAAEAPLLDKKWLTFALAIYT-Ac (SEQ ID NO:3)

Am-MAATTIGGAAAAEAAPLLDKK-Ac (SEQ ID NO:10)

and functional variants thereof. Hydropathy analysis of the pmoC sequence suggests that this subunit comprises of at least seven transmembrane helices, and we have shown that this particular signal peptide allows the insertion and correct folding of membrane proteins containing a similar number of transmembrane helices. The pmo system also has another known signal peptide originated from the pmoB subunit of the structural genes. Constructs containing this signal peptide sequence may also be created. Convenient cloning sites may be engineered either at the end of the leader peptide length or at the site of the signal peptide cleavage. Leader peptides containing 20 or 30 amino acid fragment of the nascent pmoC N-terminus may be used to direct membrane insertion. Variants of membrane targeting sequences may be generated by any of the techniques described above for promoters. The functionality of variants may be tested by measuring the yield of the recombinant membrane proteins obtained. Alternatively, the relative distribution of the protein in the membrane and soluble fractions may be measured. The coding sequences for archaeal membrane proteins contain a signal peptide that may be recognized by the membrane translocation machinery in methanotrophs and used as a membrane targeting sequence. In certain embodiments, a functional variant of SEQ ID NO:3 comprises an amino acid sequence that is at least 80% identical to that of SEQ ID NO:3, optionally at least 90%, at least 95% or at least 99% identical.

A membrane targeting sequence may be considered operably linked to an expressible nucleic acid provided that a significant portion of the nucleic acid expression product, such as at least 10% and preferably at least 50%, is targeted to a membrane. In many instances, an operable linkage is one in which the amino acid sequence encoded by the membrane targeting sequence is expressed as a fusion with the polypeptide to be targeted.

In certain embodiments, an expression construct of the invention comprises a transcriptional terminator. A transcriptional terminator is a cis-acting sequence that causes an RNA polymerase to discontinue transcription of a nucleic acid. The exact length of a transcript is not generally significant and therefore a transcriptional terminator may be positioned at a wide range of positions relative the expressed nucleic acid and still have the desired effect of causing the transcript to terminate. Accordingly, a transcriptional terminator is operably linked to an expressed nucleic acid provided that it mediates, or is compatible with, expression of the nucleic acid at a desired level. For example, an operably linked transcriptional terminator should not allow termination of the transcript at a length that is so long that it prevents the achievement of desired transcript levels, and an operably linked transcriptional terminator should not cause premature termination (i.e. 3' truncation} of the transcript. In embodiments where an expression construct of the invention is to be positioned among many other transcribed genes, such as on a chromosome or on a phage genome, the presence or absence of a transcriptional terminator in the expression construct will typically have little effect because transcript termination can be provided by other terminators that are endogenous to the chromosome or genome. In embodiments where an expression construct of the invention is to be carried in a cell as an episome (e.g. on an autonomously replicating plasmid), the presence of a transcriptional terminator may improve the level of expression that is achieved. Exemplary transcriptional terminators include the sequences of SEQ ID Nos:6 or 8 and functional variants thereof. In certain embodiments, functional variants of a transcriptional terminator of SEQ ID Nos: 6 or 8 include sequences that are at least 80% identical to the corresponding sequence, and optionally at least 90%, 95% or at least 99% identical to the corresponding sequence.

The expressible nucleic acid to be included in an expression construct of the invention may be any nucleic acid of interest. The nucleic acid need not encode a polypeptide, and it may also encode a series of distinct polypeptides in a manner analogous to a polycistronic operon. In certain preferred embodiments, the nucleic acid to be expressed encodes a membrane protein such as an integral membrane protein and, optionally, a multipass membrane protein. Exemplary types of membrane protein include transmembrane receptors, channels, transporters and membrane-bound metabolic enzymes. In some embodiments, the nucleic acid to be expressed is heterologous with respect to the promoter, the membrane targeting sequence or the transcriptional terminator. In certain embodiments the nucleic acid of interest encodes an RNA with an activity, such as a ribozyme, an antisense RNA, an RNA that forms part of a ribonucleoprotein or a regulatory RNA. The nucleic acid to be expressed using a method and/or a vector of the present invention is referred to herein as an expressible nucleic acid.

The genetic code for translating an RNA into a polypeptide is degenerate, meaning that there are multiple three-letter nucleic acid codons for most amino acids. Each of these codons are not used at an equal frequency in all organisms. For example, certain codons will be common in mammals and rare in bacteria. Production of protein may be decreased if one or more of the codons in an expressible nucleic acid are rare with respect to the cell that the nucleic acid is expressed in. Accordingly, the sequence of an expressible nucleic acid encoding a polypeptide may be altered to improve expression by replacing one or more codons of the open reading frame with a codon that occurs with greater frequency in the host cell. For example, if a mammalian protein is to be expressed in a methanotroph, it may improve protein expression to replace one or more of the codons with a codon encoding the same amino acid that is more commonly used in methanotrophs. Codon usage data is available from a number of public databases, and this information may change over time as genomic sequences for each organism are completed. Exemplary codon usage tables are provided below, with the three letter codon followed by the frequency of the codon per 1000 codons.

TABLE 2

Codon Usage in Methylosinus trichosporium

| UUU | 3.4  | UCU | 1.4  | UAU | 20.6 | UGU | 2.0  |
| UUC | 46.0 | UCC | 9.8  | UAC | 13.5 | UGC | 7.8  |
| UUA | 0.0  | UCA | 1.4  | UAA | 0.0  | UGA | 3.0  |
| UUG | 4.4  | UCG | 29.4 | UAG | 0.3  | UGG | 27.7 |
| CUU | 4.4  | CCU | 2.4  | CAU | 10.1 | CGU | 11.8 |
| CUC | 32.8 | CCC | 9.5  | CAC | 12.2 | CCC | 36.8 |
| CUA | 0.7  | CCA | 0.0  | CAA | 4.7  | CGA | 3.4  |
| CUG | 45.0 | CCG | 32.5 | CAG | 26.7 | CGG | 6.4  |
| AUU | 6.4  | ACU | 1.4  | AAU | 10.8 | AGU | 0.3  |
| AUC | 47.0 | ACC | 27.0 | AAC | 14.9 | AGC | 11.2 |
| AUA | 1.7  | ACA | 2.4  | AAA | 6.1  | AGA | 2.7  |
| AUG | 21.6 | ACG | 27.0 | AAG | 40.2 | AGG | 0.3  |
| GUU | 8.5  | GCU | 12.5 | GAU | 21.0 | GGU | 4.7  |
| GUC | 35.8 | GCC | 39.6 | GAC | 38.2 | GGC | 61.5 |
| GUA | 0.3  | GCA | 1.7  | GAA | 14.5 | GGA | 6.1  |
| GUG | 27.7 | GCG | 45.6 | GAG | 48.0 | GGG | 3.0  |

TABLE 3

Codon Usage in Homo sapiens

| UUU | 16.9 | UCU | 14.6 | UAU | 12.0 | UGU | 9.9  |
| UUC | 20.4 | UCC | 17.4 | UAC | 15.6 | UGC | 12.2 |
| UUA | 7.2  | UCA | 11.7 | UAA | 0.7  | UGA | 1.3  |
| UUG | 12.5 | UCG | 4.5  | UAG | 0.6  | UGG | 12.8 |
| CUU | 12.7 | CCU | 17.3 | CAU | 10.4 | CGU | 4.7  |
| CUC | 19.4 | CCC | 20.0 | CAC | 14.9 | CGC | 10.9 |
| CUA | 6.9  | CCA | 16.7 | CAA | 11.8 | CGA | 6.3  |
| CUG | 40.2 | CCG | 7.0  | CAG | 34.6 | CGG | 11.9 |
| AUU | 15.7 | ACU | 12.8 | AAU | 16.7 | AGU | 11.9 |
| AUC | 21.5 | ACC | 19.2 | AAC | 19.5 | AGC | 19.3 |
| AUA | 7.1  | ACA | 14.8 | AAA | 24.0 | AGA | 11.5 |
| AUG | 22.3 | ACG | 6.2  | AAG | 32.9 | AGG | 11.4 |
| GUU | 10.9 | GCU | 18.6 | GAU | 22.3 | GGU | 10.8 |
| GUC | 14.6 | GCC | 28.6 | GAC | 26.0 | GGC | 22.9 |
| GUA | 7.0  | GCA | 16.0 | GAA | 29.1 | GGA | 16.3 |
| GUG | 28.9 | GCG | 7.6  | GAG | 40.8 | GGG | 16.4 |

In certain embodiments, recombinant nucleic acids and expression constructs of the invention are incorporated into a larger nucleic acid structure, such as a vector, a large (e.g. 100,000 bases or larger) bacterial episome or a chromosome. Types of vectors include plasmids (e.g. broad host range plasmids, suicide plasmids or autonomously replicating plasmids), phages and transposons. Vectors may be designed to shuttle between two or more organisms (e.g. E. coli—Methylococcus shuttle vectors, yeast-bacterial shuttle vectors, broad host range plasmids and phage). Vectors may also be designed for integration into a host cell's chromosomal DNA, as in the case of many phage and suicide vectors. Suicide vectors are vectors that, with respect to one cell type, are not competent for replication and are therefore only maintained in the cell type if they integrate with another nucleic acid (e.g. a chromosome or episome) that is competent for replication. In yet further embodiments, vectors may be designed primarily for ease of cloning and propagation in a well-characterized organism such as E. coli. In certain embodiments, an integrative vector is designed so as to permit transfer or replication of the recombinant nucleic acid or expression construct into the chromosome of a host. In this instance, the recombinant nucleic acid or expression construct may be inserted into the chromosome without the accompanying vector material.

4. Cloning Vectors:

In certain aspects, the invention relates to vectors that are useful for generating and propagating any of the various recombinant nucleic acids and expression constructs disclosed herein. In certain embodiments, the vector is a cloning vector, meaning that the vector has at least one cloning site positioned in such a way as to facilitate the construction of a recombinant nucleic acid or expression construct disclosed herein. A cloning vector may have many additional properties and functionalities. In certain embodiments, a cloning vector of the invention is capable of autonomous replication in a cell having an intracytoplasmic membrane system. In further embodiments, a cloning vector of the invention is designed to integrate into the genome of a cell having an intracytoplasmic membrane system. Various expression constructs disclosed herein comprise multiple components, as in the case of expression constructs comprising at least two of the following: a promoter, a membrane targeting sequence and a transcriptional terminator. The construction of a multicomponent construct may be accomplished through multiple cloning steps using a series of cloning vectors that each facilitate the addition of one or more of the components. Accordingly, a variety of different cloning vectors having different components are contemplated.

In one embodiment, the invention relates to a cloning vector comprising one regulatory element selected from among the following: a promoter suitable for expression of a nucleic acid in a cell having an intracytoplasmic membrane system, a membrane targeting sequence and a transcriptional terminator, and further comprising a cloning site positioned such that a nucleic acid of interest inserted at the cloning site is operably linked to the regulatory element.

In a further embodiment, the invention relates to a cloning vector comprising a membrane targeting sequence, a promoter suitable for expression of a nucleic acid in a cell having an intracytoplasmic membrane system and a cloning site positioned such that an expressible nucleic acid inserted at the cloning site is operably linked to the promoter and the membrane targeting sequence. Optionally, the cloning vector further comprises a transcriptional terminator sequence positioned such that an expressible nucleic acid inserted at the cloning site is operably linked to the transcriptional terminator sequence.

In yet additional embodiments, a cloning vector of the invention is a broad host range vector, such as an RK2-based vector. For example, a minimal RK2 replicon consists of the origin of vegetative replication (oriV) and the gene encoding an essential initiator protein (TrfA) that binds to iterons in oriV. Certain point mutations in the trfA gene have been shown to increase the copy numbers of the minimal RK2 replicons. Several exemplary broad host range vectors include: plasmids pDSK509, pDSK519, pRK415 (constructed by Prof. N. T. Keen at UC Riverside), or cosmids pVK100, pVK101, pVK102 (constructed by Prof. E. W. Nester at U of Washington).

In certain embodiments, cloning vectors of the invention are integrative vectors. The incorporation of the heterologous genes can occur via either homologous recombination mechanisms or through non-homologous recombination pathways. Many vehicles allowing the delivery of genes and their stable incorporation into bacterial chromosome contain transposonal elements. In one embodiment, an integrative cloning vector is based on transposon Tn5. Transposon-carrying vectors capable of delivering genes into cells having intracytoplasmic membrane structures are typically based on derivatives of the Tn5 transposon. An exemplary vector is based on Stoylar et al, M. E. (2001) *J. Bact.* 183, 1810-1812.; Lloyd, J. S., Finch, R., Dalton, H., Murrell, J. C. (1999) *Microbiology* 145, 461-470. b) Lloyd, J. S., De Marco, P., Dalton, H., Murrell, J. C. (1999) *Arch. Microbiol.* 171, 364-370; Chistoserdov, A. Y. et als. (1994) *J. Bacteriol.* 176, 4052-4065. In short, the BamHI oriT-bearing DNA fragment from plasmid pSUP201122 is inserted into the BamHI site of the cloning vector pUC 18. This BamHI fragment from the pSUP2011 contains the mobilization Mob sequence that includes the oriT acting as a recognition site for certain trans active RP4 transfer function. The trans acting mobilization functions is provided during conjugation by the donor *E. coli* strain S17-1 which contains the chromosomally integrated RP4 plasmid. This strain is kanamycin sensitive and very efficient in DNA uptake. Subsequently, the EcoRI-AlwNI fragment containing the oriV of the resulting vector is replaced by the same fragment from plasmid pAT153 (a derivative of the plasmid pBR322). The KmR gene from pUC4K will then used to replace the ApR gene. This exemplary vector acts as a transposon carrier replicon for transposon insertion into the genome of methanotrophs in which the vector can be mobilized but not stably maintained. The insert containing the promoter/signal sequence/recombinant gene without terminator transcriptional fusion will be introduced into the construct at appropriate restriction site. This vector can be used to integrate the expression cassette into the chromosome at the site of the promoter fragment as a single cross-over insertion. For example, a non-homologous recombination integrative vector may be generated by using the integrative vector pSUP2021 and the pRK2013 vector as the helper plasmid (Simon, R., et al, (1983) *Bio/Technology* 1, 784-791, Figurski, D. H., et al. (1979) *Proc. Natl. Acad. Sci. USA* 77, 7347-7357. The integrative pSUP2021 vector and related plasmids are able to insert the Tn5 transposon containing the phenotype conferring selection marker gene at random location in the chromosome of methanotrophs. Hence by cloning into the transposon Tn5 the expression insert, another vector for heterologous gene expression is generated. The transposon segment of the pSUP2021 is replaced by minitransposons. These minitransposons retain primarily those elements needed for transposition, such as the insertion sequence and the transposase gene. In a minitransposon, these elements are arranged such that the transposase gene is adjacent to but outside of the mobile DNA segment, such that the transposase gene is not itself copied during transposition. The advantage of using minitransposons is that once inserted, the transposons are inherited in a stable fashion and do not provoke DNA rearrangement or other genetic instability since they lack the cognate transposase gene. Furthermore, the loss of the transposase gene means that the host cell does not become immune to further rounds of transposition. This will allow the organisms to be re-engineered by the same system, provided that subsequent transposons contain distinct selection markers. Constructs containing these minitransposons can be readily obtained from the pUT plasmid series created by Prof. K. N. Timmis de Lorenzo, V., Timmis K. N. (1994) *Methods Enzymol.* 235, 386-405. A schematic arrangement of a transposon construct is shown in FIG. 3.

In additional embodiments, a cloning vector of the invention is a bacteriophage-based vector. The construction of such vectors is described above.

Cloning sites for cloning vectors are well known in the art and include, for example, restriction sites, topoisomerase recombination sites, recombinase sites and transposase sites. For example, the Cre-lox recombinase system can facilitate cloning. Cre, in certain forms, is a 38-kDa site-specific recombinase from bacteriophage P1 that mediates recombination between DNA sequences at specific loci, called loxP sites. These sites consist of two 13-bp inverted repeats separated by an 8-bp spacer region that provides directionality to the recombination reaction; the fixed directionality of this 8-bp region keeps the orientation and reading frame of a nucleic acid of interest intact following transfer to another vector. An exemplary Cre-lox system that may be adapted for use with certain nucleic acid constructs and cloning vectors of the invention is the Creator™ Gene Clonning & Expression System (BD Biosciences Clontech, Palo Alto, Calif.). The TOPO® cloning systems (Invitrogen Corp., Carlsbad, Calif.) are an example of a topoisomerase-based system that may be adapted for use with certain nucleic acid constructs and cloning vectors of the invention. Topoisomerase I-mediated cloning uses the reaction mediated by, for example, Vaccinia DNA topoisomerase I to join PCR-amplified DNA fragments into plasmid vectors. PCR fragments have 5' hydroxyl residues from the primers used for the amplification reaction, and therefore are an ideal substrate for the topoisomerase ligation reaction. The topoisomerase I links to the vector through the 3' phosphate (P) of the incised strand. The PCR product has single 3' A overhangs (A). Vaccinia DNA topoisomerase I, to both cleave and rejoin DNA strands with a high sequence specificity. The enzyme, a 314-amino-acid virus-encoded eukaryotic type I topoisomerase, binds to duplex DNA and cleaves the phosphodiester backbone of one strand at a consensus pentapyrimidine element 5'-(C/T)CCTT in the scissile strand. In the cleavage reaction, bond energy is conserved by formation of a covalent adduct between the 3' phosphate of the incised strand and a tyrosyl residue (Tyr-274) of the protein. The covalent complex can reclose across the same bond originally cleaved (as occurs during DNA relaxation) or it can combine with a heterologous acceptor DNA that has a 5' hydroxyl tail complementary to that of the adduct, and thereby create a recombinant molecule.

In certain embodiments, a cloning site may be designed for compatibility with so-called TA cloning, based on the tendency of Taq polymerase to generate 3' T overhangs on amplified PCR products. A vector for TA cloning need only have a restriction site that, when digested, provides a 5' A for ligation with the 3' T of a Taq-amplified nucleic acid. SrfI is an example of a restriction enzyme with this property. The PCR-Script® cloning kits (Stratagene, La Jolla, Calif.) allow the efficient cloning of PCR fragments with a high yield and a low rate of false positives. PCR products are incubated with one of the predigested PCR-Script cloning vectors, Srf I and T4 DNA ligase. Using the restriction enzyme in the ligation reaction maintains a high-steady-state concentration of digested vector DNA and allows the use of nonphosphorylated, unmodified PCR primers. The ligation efficiency of blunt-ended DNA fragments is increased by the simultaneous, opposite reactions of the Srf I restriction enzyme and T4 DNA ligase on nonrecombinant vector DNA.

In certain embodiments, circular nucleic acid vectors of the invention may be provided in a linearized form. Furthermore, in the case of topoisomerase cloning sites, the vector may be provided with covalently bonded topoisomerase.

In general, vectors can be constructed using techniques well known in the art (Sambrook et al., 1989, Molecular Clonging, A Laboratory Manual, Cold Spring Harbor Press, Plainview N.Y.; Ausubel et al., 1989, Current Protocols in Molecular Biology, John Wiley & Sons, New York N.Y.). Briefly, the nucleic acid sequence of interest is placed in operable combination with transcription and, if protein expression is desired, translation regulatory sequences. Regulatory sequences include initiation signals such as start (i.e., ATG) and stop codons, promoters which may be constitutive (i.e., continuously active) or inducible, as well as enhancers to increase the efficiency of expression, and transcription termination signals. Expression vectors may become integrated into the genome of the host cell into which they are introduced, or are present as unintegrated vectors. Typically, unintegrated vectors are transiently expressed and regulated for several hours (eg., 72 hours) after transfection.

5. Kits

In certain embodiments, the invention relates to kits comprising a recombinant nucleic acid of the invention and one or more additional components. Together, the components constitute a functional unit for a given purpose, such as, for example, cloning a nucleic acid, generating an expression construct or transferring an expression construct onto a vector that is suitable for introduction into a cell having an intracytoplasmic membrane system. Exemplary kit components may include: a cloning enzyme, such as a ligase, a recombinase, a transposase, a topoisomerase or a restriction enzyme, an enzyme buffer, competent cells (cells that have been prepared for transformation with a nucleic acid), an oligonucleotide for use in an amplification procedure such as PCR, an oligonucleotide for use in a sequencing reaction, media components for culturing cells and instructions. Oligonucleotides may be designed to be complementary to a portion of the recombinant nucleic acid component. In preferred embodiments, the recombinant nucleic acid is a cloning vector of the invention. Optionally, the cloning vector is provided in a linearized form. Kits may additionally comprise reagents for the purification of a protein. Exemplary reagents include a cell lysis buffer, an affinity purification reagent that corresponds to any affinity purification tag that might be present on the cloning vector, Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation. The individual components of the kit may or may not be from the same supplier, or manufacturer. A component can either be purchased as a part of the kit, or generated by user "in-house" according to the instruction of the kit.

EXEMPLIFICATION

The invention now being generally described, it will be more readily understood by reference to the following examples, which are included merely for purposes of illustration of certain aspects and embodiments of the present invention, and are not intended to limit the invention.

Example 1

The pmo promoters (pmo1 and pmo2) were isolated from genomic DNA of *Methylococcus capsulatus* (Bath) using the physical map of the pmo loci as a guide. DNA fragments containing the promoters obtained by PCR amplification of genomic DNA were cloned into the pMOS-Blue cloning vector (Amersham Pharmacia) using the EcoRV blunt-end cloning site. From the nucleotide sequence of the 5' flanking region of pmoC, new DNA fragments containing the promoters and the translated 5' leader sequence of the pmoC subunit were amplified from genomic DNA and cloned into pMOS-Blue cloning vector. Plasmids containing the promoter and the leader sequence fragment in proper orientation such that the upstream sequence of the promoter was flanked by a unique SaII site and the leader sequence was terminated at a unique BamHI site were identified. An alternative construction was these unique cloning sites were introduced into the DNA fragment by PCR method. Another unique restriction site, NdeI, preceding the BamHI site was engineered at a pre-determined location around the end of the leader sequence. The transcriptional terminator sequences for the pmo1 and pmo2 loci were also cloned from genomic DNA using similar protocols. The cloned DNA fragments containing the transcriptional terminators also include a portion of the C-terminus and the stop codon of the pmo B subunit. Unique restriction sites (KpnI and EcoRI) were then engineered at the beginning and at the end of these fragments by PCR technique.

The model receptor, $\beta_2$-adrenergic receptor coding sequence was obtained from the plasmid pTF3 purchased from American Type Culture Collection. PCR amplification was used to obtain the coding sequence of the receptor, eliminating the untranslated 5' region flanking the start codon and the polyadenylation sequence that follows the stop codon. Unique restriction sites were engineered at the start codon (NdeI site) and after the stop codon (BarnHI) to facilitate efficient cloning of the receptor coding sequence into the expression vector. Furthermore, rare arginine codons (AGG and AGA) present in the receptor coding sequence were changed into common bacterial arginine codons (CGG, CGT, and CGC) by site directed mutagenesis. There are a total of 7 rare arginine codons in the receptor sequence. As a result, a synthetic $\beta_2$ receptor was created. for maximum translation efficiency in methanotrophs. Furthermore, a 6xHis tag sequence was also introduced at the C-terminus of the synthetic $\beta_2$ receptor coding sequence to facilitate the purification of the recombinant protein later.

The synthetic $\beta_2$ receptor gene with the flanking NdeI/Bam/HI sites was cloned into the constrict containing the pmo promoter using the unique NdeI and BamHI restriction sites that allow proper in-frame orientation of the coding insert. The entire DNA fragment containing the promoter, the signal peptide, and the receptor coding sequence (the SAlI/BamHI DNA fragment) was then cloned into a broad host-range vector, pDSK509, a gift from Prof. N. T. Keen of UC Riverside using the SalI/BamHI sites present in the polylinker region of this vector. The DNA fragment containing the corresponding transcriptional terminator was also cloned into this vector using the KpnI/EcoRI sites in the polylinker region of this vector. A schematic presentation of the entire construct using pmo1 promoter and terminator is shown in FIG. 2.

The expression vector was transformed into methanotrophs (in this case, *Methylococcus capsulatus* (Bath)) either by conjugation or by electroporation methods. The transformed cells were cultured on agar plate containing he NMS medium and the selection market, kanamycin (50 mg/L). Colonies observed on the transformation plates were picked and grown in liquid NMS medium containing kanamycin (50 mg/L). The medium was supplemented with FeEDTA (5 µM) to promote the expression of the soluble methane monooxygenase and to suppress the expression of the particulate methane monooxygenase. After the cell density reached an OD of 0.6-0.8, copper sulfate and CuEDTA were added to the growth medium to raise the copper ion concentration to a minimum of 20 µM. The culture was continued for at least another 24 hrs before harvesting. The cells were washed, resuspended in buffer and lysed by French press. The cell lysate was centrifuged at 15,000 rpm to remove cellular debris. The supernatant was collected and centrifuged at 45,000-65,000 rpm for at least one hour to pellet the membrane fractions. The isolated membrane fractions were subjected to dodecyl maltoside solubilization (0.01-0.05% weight/volume). The solubilized materials were centrifuged at 18,000 rpm to remove unsolubilized fractions. The clear supernatant was then subjected to affinity chromatography (metal affinity chromatography for version with the 6xHis-tag or ligand affinity chromatography for version without the 6xHis-tag) to purify the recombinant solubilized receptor.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Such references include the following:
1. Anthony, C. *The Biochemistry of Methanotrophs* (1982).
2. Hansen, R. S., Hanson, T. E. *Methanotrophic Bacteria. Microbiol. Rev.* 60 (1996) 439-471.
3. Lipscomb, J. D. (1994) *Annu. Rev. Microbiol.* 48, 371-399.
4. Nguyen, H. -H. T., Shiemke, A. K., Jacobs, S. J., Hales, B. J., Lidstrom, M. E., Chan, S. I. (1994) *J. Biol. Chem.* 269, 14995-15005.
5. Nielsen, A. K., Gerdes, K., Murrell, J. C. (1997) *Mol. Microbiol.* 25, 399-409.
6. a) Fox, B. G., Froland, W. A., Jollie, D. R., Lipscomb, J. D. (1990) *Methods Enzymol.* 188, 191-202. b) Pilkington, S. J., Dalton, H. (1990) *Methods Enzymol.* 188, 181-190.
7. Nguyen, H. -H. T., Elliott, S. J., Yip, J. H. -K., Chan, S. I. (1998) *J. Biol. Chem.* 273, 7957-7966.
8. Hollenberg, C. P., Gellissen, G. (1997) *Curr. Opin. Biotech.* 5, 554-560.
9. Edwards, A. M., Arrowsmith, C. H., Christendat, D., Dharamsi, A., Friesen, J. D., Greenblatt, J. F., Vedadi, M. (2000) *Nature Struct. Biol.* 7, Supp. 970-972.
10. Stoylar, S., Franke, M., Lidstrom, M. E. (2001) *J. Bact.* 183, 1810-1812.
11. Preusch, P. C., Norvell, J. C., Cassatt, J. C., Cassman, M. (1998) *Nature Stuct. Biol.* 5, 12-14.
12. a) Knauf, V. C., Nester, E. W. (1982) *Plasmid* 8, 45-54. b) Keen, N. T., Tamaki, S., Kobayashi, D., Trollinger, D. (1988) *Gene* 70, 191-197.
14. Gilbert, B., McDonald, I. R., Finch, R., Stafford, G. P., Nilsen, A. K., Murrell, J. C. (2000) *Applied & Environ. Microbiol.* 66, 966-975.
15. Lloyd, J. S., Finch, R., Dalton, H., Murrell, J. C. (1999) *Microbiology* 145, 461-470. b) Lloyd, J. S., De Marco, P., Dalton, H., Murrell, J. C. (1999) *Arch. Microbiol.* 171, 364-370.
16. Stoylar, S., Costello, A. M., Peeples, T. L., Lidstrom, M. E. (1999) *Microbiology* 145, 1235-1244.
17. a) Tyutikov, F. M., Bespalova, I. A., Rebentish, B. A., Aleksandrushkina, N. N., Krivisky, A. S. (1980) *J. Bacteriol.* 144, 375-381. b) Tyutikov, F. M., Yesipove, V. V., Rebentish, B. A., Bespalove, I. A., Aleksandrushkina, N. N., Galchenko, V. V., Tikhonenko, A. S. (1983) *Applied & Environ. Microbiol.* 46, 917-924.
18. Gallagher, P. G., Forget, B. G. (1995) *J. Biol. Chem.* 72, 452-455.
19. Samrau, J. D., Chistoserdov, A., Lebron, J. and 7 other authors (1995) *J. Bacteriol.* 177, 3071-3079.
20. Blatny, J. M., Brautaset, T., Winther-Larsen, H. C., Karunakaran, P., Valla, S. (1997) *Plasmid* 38, 35-51.
21. Chistoserdov, A. Y., Chistoserdova, L. V., McIntire, W. S., Lidstrom, M. E. (1994) *J. Bacteriol.* 176, 4052-4065.
22. Simon, R., Priefer, U., Puhler, A. (1983) *Bio/Technology* 1, 784-791.
23. Figurski, D. H., Hellinski, D. R. (1979) *Proc. Natl. Acad. Sci. USA* 77, 7347-7357.
24. de Lorenzo, V., Timmis K. N. (1994) *Methods EnzymoL* 235, 386-405.
25. Whittenbury, R., Dalton, H. The Methylotrophic Bacteria in *The Prokaryotes*, pp. 894-902. Edited by Star, M., Stolp, H., Truper, H., Balows, A., Schlegel, H. Berlin: Springer.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed:

1. A methanotrophic bacterium comprising an expression construct encoding a membrane protein that is foreign to the methanotrophic bacterium, said expression construct comprising:
   a. an expressible nucleic acid sequence comprising a membrane targeting sequence coding sequence operably linked to a coding sequence for the membrane protein; and
   b. a pmo promoter operably linked to the expressible nucleic acid sequence, wherein the pmo promoter comprises a nucleic acid sequence selected from the group consisting of: SEQ ID NO: 1, SEQ ID NO: 2, SEQ ID NO: 4 and SEQ ID NO: 7.

2. The methanotrophic bacterium of claim 1, wherein the membrane-targeting sequence is a membrane-targeting leader sequence, and wherein said membrane targeting sequence coding sequence is positioned 5' relative to the expressible nucleic acid sequence.

3. The methanotrophic bacterium of claim 2, wherein the leader sequence is encoded by the nucleic acid sequence of SEQ ID NO: 5.

4. The methanotrophic bacterium of claim 1, wherein the membrane-targeting sequence is a leader sequence from a particulate methane monooxygenase subunit.

5. The methanotrophic bacterium of claim 4, wherein the leader sequence comprises an amino acid sequence selected from the group consisting of: SEQ ID NO: 3, SEQ ID NO: 9, and SEQ ID NO: 10.

6. The methanotrophic bacterium of claim 1, further comprising a transcriptional terminator sequence operably linked to the expressible nucleic acid sequence.

7. The methanotrophic bacterium of claim 6, wherein the transcriptional terminator sequence comprises a nucleic acid sequence selected from the group consisting of: SEQ ID NO: 6, and SEQ ID NO: 8.

8. The methanotrophic bacterium of claim 1, wherein the expression construct is a vector.

9. The methanotrophic bacterium of claim 8, wherein the vector is selected from the group consisting of: a plasmid, a cosmid, a suicide vector and a recombinant phage.

10. The methanotrophic bacterium of claim 1, wherein the expression construct further comprises an origin of replication and/or an antibiotic resistance cassette.

11. The methanotrophic bacterium of claim 1, wherein the methanotrophic bacterium has an intracytoplasmic membrane system.

12. The methanotrophic bacterium of claim 1, wherein the methanotrophic bacterium is selected from the group consisting of: a *Methylococcus capsulatus*, a *Methylosinus trichosporium* and a *Methylocystis* sp.

13. A method for producing the membrane protein of claim 1, comprising culturing the methanotrophic bacterium, under conditions suitable for production of the membrane protein, thereby producing the membrane protein.

14. The method of claim 13, wherein culturing the cell under conditions suitable for production of the polypeptide comprises exposing the cell to copper(II).

15. The method of claim 14, wherein the copper(II) is provided at a concentration ranging from about 5 µM to about 50 µM.

16. The method of claim 13, further comprising: preparing a partially purified polypeptide composition comprising the membrane protein.

17. The method of claim 16, further comprising: preparing a purified polypeptide composition comprising the membrane protein.

18. A methanotrophic bacterium comprising an expression construct encoding a membrane protein that is foreign to the methanotrophic bacterium, said expression construct comprising:
   a. an expressible nucleic acid sequence comprising a coding sequence for a leader sequence for a particulate methane monooxygenase subunit operably linked to a coding sequence for the membrane protein, and wherein the leader sequence targets the membrane protein to an intracytoplasmic membrane; and
   b. a viral coat protein promoter, a bacteriophage promoter, or an *E. coli lac* promoter operably linked to the expressible nucleic acid sequence.

19. The methanotrophic bacterium of claim 18, wherein said coding sequence for said leader sequence is positioned 5' relative to the expressible nucleic acid sequence.

20. The methanotrophic bacterium of claim 18, wherein the leader sequence comprises an amino acid sequence selected from the group consisting of SEQ ID NO:3 and SEQ ID NO:10.

21. The methanotrophic bacterium of claim 18, further comprising a transcriptional terminator sequence operably linked to the expressible nucleic acid sequence.

22. The methanotrophic bacterium of claim 21, wherein the transcriptional terminator sequence comprises a nucleic acid sequence selected from the group consisting of: SEQ ID NO: 6, and SEQ ID NO: 8.

23. The methanotrophic bacterium of claim 18, wherein the expression construct is a vector.

24. The methanotrophic bacterium of claim 23, wherein the vector is selected from the group consisting of: a plasmid, a cosmid, a suicide vector and a recombinant phage.

25. The methanotrophic bacterium of claim 18, wherein the expression construct further comprises an origin of replication and/or an antibiotic resistance cassette.

26. The methanotrophic bacterium of claim 18, wherein the methanotrophic bacterium has an intracytoplasmic membrane system.

27. The methanotrophic bacterium of claim 18, wherein the methanotrophic bacterium is selected from the group consisting of: a *Methylococcus capsulatus*, a *Methylosinus trichosporium* and a *Methylocystis* sp.

28. A method for producing the membrane protein of claim 18, comprising culturing the methanotrophic bacterium, under conditions suitable for production of the membrane protein, thereby producing the membrane protein.

29. The method of claim 28, further comprising: preparing a partially purified polypeptide composition comprising the membrane protein.

30. The method of claim 29, further comprising: preparing a purified polypeptide composition comprising the membrane protein.

* * * * *

SEQUENCE LISTING

<160> NUMBER OF SEQ ID NOS: 10

<210> SEQ ID NO 1
<211> LENGTH: 56
<212> TYPE: DNA
<213> ORGANISM: Methylococcus capsulatus

<400> SEQUENCE: 1

-continued

```
ccctgcgtca aaatgtcgca gattttctt gacagtttgg gggagggtga tagatc        56
```

<210> SEQ ID NO 2
<211> LENGTH: 55
<212> TYPE: DNA
<213> ORGANISM: Methylococcus capsulatus

<400> SEQUENCE: 2

```
cctgcgtcaa aatgacgcag attttcctg acagcctcgg gttgggtgat agact          55
```

<210> SEQ ID NO 3
<211> LENGTH: 30
<212> TYPE: PRT
<213> ORGANISM: Methylococcus capsulatus

<400> SEQUENCE: 3

```
Met Ala Ala Thr Thr Ile Gly Gly Ala Ala Ala Glu Ala Pro Leu
1               5                   10                  15

Leu Asp Lys Lys Trp Leu Thr Phe Ala Leu Ala Ile Tyr Thr
            20                  25                  30
```

<210> SEQ ID NO 4
<211> LENGTH: 1556
<212> TYPE: DNA
<213> ORGANISM: Methylobacter capsulatus

<400> SEQUENCE: 4

```
gtcgactggg caccagccgg atgcgtccgt caaccccgac tgttccgcca agaactccgg    60
ccttctgtgg cgggatgacg ttgagcacat cggcacagaa agtgtcgaac tcggtttcga   120
cggttcgccc ggcggcatcg atccgctcca gccgtccctc tttttccgag gaaacccatt   180
ccaccatgtc tccgtagagt cgcgccaggg cctgctcgaa tgccggctgc ttggaaaacc   240
gggtcttggc atcgagtatc aggatcttgg agcggggttt gtgcttttc atgtaatagg   300
cgatgagcga ggcgcgttcg tagggggcag gcggacaacg ataggagaa ggtggtgcgg   360
tgatcagaac caggccgccg tcgggcatcg cgcggatctg ccgggcgagc aaagcggtct   420
gggggccggc cttccaggca tggggaacga accggctcgc cgcctcgtca tagcccatta   480
tcgcctccca gcgaaagtcg atgccggggg agaggactag cctgtcgtag gtgacctcgg   540
caccatcgtt cagtatcaca cgccgtcgct gccgatccag gcgggcgacc cgggcggtta   600
cctttcctat atccagctcc cgccgcaacc agtcataaga ccgcgcgaga gtccccatgt   660
ccccgaggcc ggcgactgct tcgttcgatc cggggcagga aagataagtc tcctgcggtt   720
cgatcaatgt gatcgtcaga ccgggattca tctgcttcag atagcgggcg gccgtggcac   780
cgccataacc gccaccgacg accacgaccg gccgcctgag cgaagacctt gccggaagcg   840
cagccaccca gtcccagccc atgccgcaga ctgccagcag gcgcaggaac gccgccggc    900
ggatcatggc ctctttccca gaagccggc gatcgcttca atgtcctggt cgtgagtcc     960
ggcagcgatc cggttcatga ccgtgcccga tcttttcct tcacggtact cccgcaacag   1020
agatgccatc tccttcgcat cgaagcggcg taacgatgcc ggttcgggaa tctgctcctc   1080
ctcgtcggca tggcagccga ggcaaccgag cgcagccaaa accatgtccg gttttcggc    1140
ccgggccggg aaacagagag cgacagcgat cgtaccgatc tggacgcgtc tcacaaacga   1200
caaaacgtca cgatgggtgt tcggtagctg agtcacgggg atttgtagaa gtataggacc   1260
gacggatttt atgcaagcat gtcgctttga ccaagccggg attccatgga agggatgtca   1320
tcgggagagt tatttatgtc gttgattat aagaaactac ccctgcgtca aatgtcgca    1380
```

-continued

```
gattttctt gacagtttgg gggagggtga tagatcctcc accgatggac cggtaccgcc    1440
tctgttgcgg ggtccatgaa atgcccgtta gaggcagaac cgatagggaa ttagagaagc   1500
gggcgtcggc gccgaatgcc ggcccctgtc aaccatcact ttaggaggaa caaaca       1556
```

<210> SEQ ID NO 5
<211> LENGTH: 90
<212> TYPE: DNA
<213> ORGANISM: Methylococcus capsulatus

<400> SEQUENCE: 5

```
atggcagcaa caaccattgg tggtgcagct gcggcggaag cgccgctgct ggacaagaag    60
tggctcacgt tcgcactggc gatttacacc                                     90
```

<210> SEQ ID NO 6
<211> LENGTH: 189
<212> TYPE: DNA
<213> ORGANISM: Methylococcus capsulatus

<400> SEQUENCE: 6

```
tttcgccggt ctgctgttct tcttcgacgc cactggcaac cgccaggtcg tccagatcga    60
cgcaccgctg atcccgtcgt tcatgtaatc gcctggggga gtccttcggg actccccagc   120
cggcggtcaa cgccaaaacc cccggccggc aacggtcggg ggttttttat tctggtctgg   180
tttgtgttc                                                           189
```

<210> SEQ ID NO 7
<211> LENGTH: 291
<212> TYPE: DNA
<213> ORGANISM: Methylococcus capsulatus

<400> SEQUENCE: 7

```
aatcctgctg gtcgcttgac cctcgtgtcc ggcgtacgcc ggacacgatc acggtctgtc    60
gcaagccgct tgttgatctg gactccttcc cagaacgagc gcagcggagc ctcccgttcc   120
gcgccgtcca ttctcttttt catccaagtg cccggctcat gaggtcggct cacgaggctg   180
agcctgcgtc aaaatgacgc agattttcct gacagcctcg ggttgggtga tagactgcga   240 ccccaccaagg ggccggccaa cccgtgggcg cggctctgag gggcggcaag g           291
```

<210> SEQ ID NO 8
<211> LENGTH: 287
<212> TYPE: DNA
<213> ORGANISM: Methylococcus capsulatus

<400> SEQUENCE: 8

```
tcgcctgggg gagtccttcg ggctcccct gccggcggtc aacgccaaaa cccccggccg     60
gcaacggtcg ggggtttttt tatcggctgg atttagacgt tcaggggcg acgatcgtca    120 agcaacaagg ccccaccagg ccggggcctt gtcgtcgagc gtcggcggcg ccgtcagccc   180
tcggcggttc gcgaagcctt cttgcgctcg tgttcctgca ggagcttctt gcggatgcga   240
atgctctgag gggtcacttc cacgagttca tcgtcgtcga tgaattc                 287
```

<210> SEQ ID NO 9
<211> LENGTH: 28
<212> TYPE: PRT
<213> ORGANISM: Flavobacterium sp.

<400> SEQUENCE: 9

```
Met Gln Thr Arg Arg Val Val Leu Lys Ser Ala Ala Ala Gly Thr Leu
1               5                   10                  15

Leu Gly Gly Leu Ala Gly Cys Ala Ser Val Ala Gly
            20                  25

<210> SEQ ID NO 10
<211> LENGTH: 21
<212> TYPE: PRT
<213> ORGANISM: Methylobacter capsulatus

<400> SEQUENCE: 10

Met Ala Ala Thr Thr Ile Gly Gly Ala Ala Ala Ala Glu Ala Ala Pro
1               5                   10                  15

Leu Leu Asp Lys Lys
            20
```